United States Patent
Kim et al.

(10) Patent No.: US 10,053,481 B2
(45) Date of Patent: Aug. 21, 2018

(54) TRANSITION METAL COMPOUND, TRANSITION METAL CATALYST COMPOSITION FOR POLYMERIZING OLEFIN, CONTAINING SAME, AND METHOD FOR PREPARING ETHYLENE HOMOPOLYMER OR COPOLYMER OF ETHYLENE AND ALPHA-OLEFIN BY USING SAME

(71) Applicant: SABIC SK NEXLENE COMPANY PTE. LTD., Singapore (SG)

(72) Inventors: Sun Young Kim, Daejeon (KR); Dong Cheol Shin, Daejeon (KR); Sang Ick Lee, Daejeon (KR); Ki Nam Chung, Daejeon (KR); Sung Seok Chae, Daejeon (KR); Yonggyu Han, Daejeon (KR)

(73) Assignee: SABIC SK NEXLENE COMPANY PTE. LTD., Singapore (SG)

( * ) Notice: Subject to any disclaimer, the term of this patent is extended or adjusted under 35 U.S.C. 154(b) by 0 days.

(21) Appl. No.: 15/314,459

(22) PCT Filed: May 28, 2015

(86) PCT No.: PCT/KR2015/005369
§ 371 (c)(1),
(2) Date: Nov. 28, 2016

(87) PCT Pub. No.: WO2015/183017
PCT Pub. Date: Dec. 3, 2015

(65) Prior Publication Data
US 2017/0204129 A1     Jul. 20, 2017

(30) Foreign Application Priority Data

May 29, 2014 (KR) .......................... 10-2014-0064935
May 27, 2015 (KR) .......................... 10-2015-0073638

(51) Int. Cl.
| | | |
|---|---|---|
| C08F 4/6592 | (2006.01) | |
| C08F 210/16 | (2006.01) | |
| C08F 110/02 | (2006.01) | |
| C07F 17/00 | (2006.01) | |
| C08F 10/02 | (2006.01) | |

(52) U.S. Cl.
CPC ............ *C07F 17/00* (2013.01); *C08F 4/6592* (2013.01); *C08F 10/02* (2013.01); *C08F 110/02* (2013.01); *C08F 210/16* (2013.01); *C08F 2420/01* (2013.01); *C08F 2800/20* (2013.01)

(58) Field of Classification Search
CPC .... C07F 17/00; C08F 4/6592; C08F 4/65908; C08F 4/65912; C08F 110/02; C08F 210/16

See application file for complete search history.

(56) References Cited

U.S. PATENT DOCUMENTS

| | | |
|---|---|---|
| 4,752,597 A | 6/1988 | Turner |
| 5,043,408 A | 8/1991 | Kakugo et al. |
| 5,079,205 A | 1/1992 | Canich |
| 5,103,030 A | 4/1992 | Rohrmann et al. |
| 5,198,401 A | 3/1993 | Turner et al. |
| 6,329,478 B1 | 12/2001 | Katayama et al. |
| 7,645,715 B2 | 1/2010 | Ok et al. |
| 2012/0041149 A1 | 2/2012 | Shin et al. |

FOREIGN PATENT DOCUMENTS

| | | |
|---|---|---|
| EP | 0320762 A2 | 6/1989 |
| EP | 0372632 A1 | 6/1990 |
| EP | 0416815 A2 | 3/1991 |
| EP | 0420436 A1 | 4/1991 |
| EP | 0842939 A1 | 5/1998 |
| JP | S6392621 A | 4/1988 |
| JP | H0284405 A | 3/1990 |
| JP | H032347 A | 1/1991 |
| JP | H08208732 A | 8/1996 |
| JP | 2002212218 A | 7/2002 |
| WO | 0005238 A1 | 2/2000 |

OTHER PUBLICATIONS

Chesnut, R. et al., "The Chemistry of Sterically Crowded Aryloxide Ligands—VII. Synthesis, Structure and Spectroscopic Properties of Some Group 4 and Group 5 Metal Derivatives of 2,6-Diphenylphenoxide," Polyhedron, vol. 6, No. 11, Available as Early as Jan. 1, 1987, 8 pages.

Thorn, M. et al., "Cationic Group 4 metal alkyl compounds containing aryloxide ligation: synthesis, structure, reactivity and polymerization studies," Journal of Organometallic Chemistry, vol. 594, No. 1-12, Dec. 5, 1999 15 pages.

Nomura, K. et al., "Synthesis of Nonbridged (Anilide)(cyclopentadienyl)titanium(IV) Complexes of the Type Cp'TiCl2 [N(2,6-Me2C6H3)(R)] and Their Use in Catalysis for Olefin Polymerization," Organometallics, vol. 21, No. 14, Jul. 8, 2002, Published Online Jun. 5, 2002, 8 pages.

Nielson, A. et al., "Molecular engineering of coordination pockets in chloro-tris-phenoxo complexes of titanium(IV)," Polyhedron, vol. 25, No. 10, Jul. 10, 2006, Published Online Feb. 28, 2006, 16 pages.

LEE, J. et al., "Facile synthesis and X-ray structures of ($\eta$5-C5Me5)Ti(OArF)3 (OArF = OC6F5, OCH2C6F5, and OCH2C6F2H3)," Journal of Organometallic Chemistry, vol. 692, No. 16, Jul. 15, 2007, Published Online May 10, 2007, 6 pages.

ISA Korean Intellectual Property Office, International Search Report Issued in Application No. PCT/KR2015/005369, dated Aug. 25, 2015, WIPO, 6 pages.

*Primary Examiner* — Caixia Lu
(74) *Attorney, Agent, or Firm* — McCoy Russell LLP

(57) ABSTRACT

Provided are a novel transition metal compound, a transition metal catalyst composition for preparing an ethylene homopolymer or a copolymer of ethylene and α-olefin, containing the same, a method for preparing an ethylene homopolymer or a copolymer of ethylene and α-olefin using the same, and an ethylene homopolymer or a copolymer of ethylene and α-olefin prepared using the same.

13 Claims, No Drawings

TRANSITION METAL COMPOUND, TRANSITION METAL CATALYST COMPOSITION FOR POLYMERIZING OLEFIN, CONTAINING SAME, AND METHOD FOR PREPARING ETHYLENE HOMOPOLYMER OR COPOLYMER OF ETHYLENE AND ALPHA-OLEFIN BY USING SAME

CROSS-REFERENCE TO RELATED APPLICATIONS

The present application is a U.S. National Phase of International Patent Application Serial No. PCT/KR2015/005369, entitled "NOVEL TRANSITION METAL COMPOUND, TRANSITION METAL CATALYST COMPOSITION FOR POLYMERIZING OLEFIN, CONTAINING THE SAME, AND METHOD FOR PREPARING ETHYLENE HOMOPOLYMER OR COPOLYMER OF ETHYLENE AND ALPHA-OLEFIN USING THE SAME," filed on May 28, 2015. International Patent Application Serial No. PCT/KR2015/005369 claims priority to Korean Patent Application No. 10-2014-0064935, filed on May 29, 2014; and to Korean Patent Application No. 10-2015-0073638, filed May 27, 2015. The entire contents of each of the above-cited applications are hereby incorporated by reference for all purposes.

TECHNICAL FIELD

The present invention relates to a novel transition metal compound; a transition metal catalyst composition for preparing an ethylene homopolymer or a copolymer of ethylene and α-olefin, containing the same; and a method for preparing an ethylene homopolymer or a copolymer of ethylene and α-olefin using the same.

BACKGROUND ART

In the prior art, so-called Ziegler-Natta catalyst consisting of a titanium or vanadium compound as a primary catalyst component and an alkylaluminum compound as cocatalyst component have been generally used for preparing ethylene homopolymers or copolymers of ethylene and α-olefin. Although a Ziegler-Natta catalytic system exhibits high activity on ethylene polymerization, the catalytic system has disadvantages in that molecular weight distribution of the produced polymer is broad due to non-uniform catalyst activation point, and especially, composition distribution thereof is not uniform in the copolymers of ethylene and α-olefin.

Since a metallocene catalyst system composed of a metallocene compound of a Group 4 transition metal in the Periodic Table of Elements, such as titanium, zirconium, hafnium, or the like, and methylaluminoxane as a cocatalyst is a homogeneous catalyst having a single catalytic active site, the metallocene catalyst system may prepare a polyethylene having a narrow molecular weight distribution and a uniform composition distribution as compared to the existing Ziegler-Natta catalyst system. For example, in European Patent Application Publication Nos. 320,762 and 372,632, or Japanese Patent Laid-Open Publication No. Sho 63-092621, Hei 02-084405, or Hei 03-002347, it was reported that ethylene may be polymerized with a high activity by activating a metallocene compound such as $Cp_2TiCl_2$, $Cp_2ZrC1_2$, $Cp_2ZrMeCl$, $Cp_2ZrMe_2$, ethylene $(IndH_4)_2ZrCl_2$, or the like, using methylaluminoxane as the cocatalyst, thereby making it possible to prepare a polyethylene having a molecular weight distribution (Mw/Mn) in a range of 1.5 to 2.0. However, it is difficult to obtain a polymer having a high molecular weight using the catalyst system, and particularly, in the case of applying the catalyst system to a solution polymerization method performed at a high temperature of 120° C. or more, a polymerization activity is rapidly decreased, and β-dehydrogenation reaction mainly occurs, such that the catalyst system is known to be not suitable for preparing a high-molecular weight polymer having a weight average molecular weight (Mw) of 100,000 or more.

Meanwhile, as a catalyst capable of having a high catalytic activity and preparing a high-molecular weight polymer in ethylene homopolymerization or copolymerization of ethylene and α-olefin under the solution polymerization conditions, a so-called geo-restrictive non-metallocene type catalyst (also referred to as a single-site catalyst) to which a transition metal is linked in a ring form has been reported. An example of a catalyst in which an amide group is linked to one cyclopentadiene ligand in a ring form has been suggested in European Patent Nos. 0416815 and 0420436, and an example of a catalyst in which a phenolic ligand as an electron donor compound is linked to a cyclopentadiene ligand in a ring form has been disclosed in European Patent No. 0842939. However, since during the synthesis of the geo-restrictive catalyst as described above, a yield of a process of a ring formation reaction between a ligand and a transition metal compound is low, there are many difficulties to commercially use such catalyst.

On the other hand, examples of a non-metallocene type catalyst that is not geo-restrictive have disclosed in U.S. Pat. No. 6,329,478 and International Publication No. WO 00/005238. In these patents, it may be confirmed that a single-site catalyst using at least one or more phosphine imine compounds as a ligand has a high ethylene conversion rate at the time of copolymerizing ethylene and α-olefin under a high-temperature solution polymerization condition at 120° C. or more. An example of a catalyst having a bisphenoxide ligand has been disclosed in U.S. Pat. No. 5,079,205 and an example of a catalyst having a bisphenoxide ligand of chelate type has been disclosed in U.S. Pat. No. 5,043,408. However, these catalysts have an excessively low activity, such that it is difficult to commercially use these catalysts for preparation of an ethylene homopolymer or a copolymer of ethylene and α-olefin, which is performed at a high temperature.

Use of an olefin based polymerization catalyst having an anilido ligand has been disclosed in Japanese Patent Laid-Open Publication Nos. 1996-208732 and 2002-212218, but an example thereof in a commercially significant polymerization temperature region has not been disclosed. In addition, a case in which the anilido ligand was used for polymerization as a non-metallocene type catalyst has been reported in [*Organometallics* 2002, 21, 3043 (Nomura et al.)]. In this case, the case was confined to a methyl group which is a simple alkyl substituent.

Therefore, it is important to secure a more competitive catalyst system capable of satisfying characteristics required in a commercial catalyst on the basis of economical efficiency, that is, an excellent high-temperature activity, excellent reactivity with higher alpha-olefin, preparation capability of a high molecular weight polymer, and the like.

DISCLOSURE

Technical Problem

In order to overcome problems in the related art, the present inventors carried out extensive studies, and found that a Group 4 transition metal catalyst containing a cyclopentadiene derivative around a Group 4 transition metal; and three aryloxide ligands having a fluorenyl group or a derivative thereof as a substituent at an ortho-position of an oxygen atom linking the ligand and the transition metal to each other, the fluorenyl group functioning as an electron donor, serving to further stabilize a catalyst system by surrounding an oxygen atom linking the ligand and the transition metal to each other, and having a chemical structure in which a substituent is easily introduced at 9-position thereof, and having a structure in which the ligands are not cross-linked has an excellent catalytic activity in polymerization of ethylene and olefins. Based on the discovery, the present inventors developed a catalyst capable of preparing a high molecular weight ethylene homopolymer or copolymer of ethylene and α-olefin with a high activity in a polymerization process performed at 60° C. or more, thereby completing the present invention.

Further, in a case of preparing a catalyst containing one cyclopentadienyl ligand and only one or two aryloxide ligands, a chemical species in which the ligand is further or less substituted is unintentionally formed, which is a limitation in preparing a high purity catalyst. Further, in the case of the catalyst containing one cyclopentadienyl ligand and only one or two aryloxide ligands, generally, a halide ion ligand or alkyl anion ligand is substituted as the other ligand. In the case of the catalyst containing the halide ion ligand, the halide ion may act as a process corrosion material, which may increase a process investment cost. A problem caused by the halide ion ligand may be solved by using a catalyst containing the alkyl anion ligand, but the catalyst containing the alkyl anion ligand has a disadvantage in that it may be easily changed by air. Therefore, an object of the present invention is to provide a single-site catalyst having a high activity for olefin polymerization in a commercial point of view by entirely substituting other ligands except for a cyclopentadienyl ligand with an aryleneoxide ligand to increase economical efficiency with respect to a process investment cost and prepare a relatively stable catalyst capable of being easily prepared, and a polymerization method capable of economically preparing an ethylene homopolymer or a copolymer of ethylene and α-olefin, which has various physical properties, using this catalyst component.

That is, an object of the present invention is to provide a transition metal compound useful as a catalyst for preparing an ethylene homopolymer or a copolymer of ethylene and α-olefin, and a catalyst composition containing the same.

Another object of the present invention is to provide an ethylene homopolymer or a copolymer of ethylene and α-olefin prepared using the transition metal compound or the catalyst composition containing a transition metal compound.

Another object of the present invention is to provide a single-site catalyst capable of being significantly economically synthesized through a simple synthesis route and having a high activity for olefin polymerization, and a polymerization method capable of economically preparing an ethylene homopolymer or a copolymer of ethylene and α-olefin, which has various physical properties, in a commercial point of view, by using the catalyst component as described above.

Technical Solution

In one general aspect, a Group 4 transition metal compound as represented by the following Chemical Formula 1 contains: a cyclopentadiene derivative around a Group 4 transition metal; and three aryloxide ligands having a fluorenyl group or a derivative thereof as a substituent at an ortho-position of an oxygen atom linking the ligand and the transition metal to each other, the fluorenyl group functioning as an electron donor, serving to further stabilize a catalyst system by surrounding the oxygen atom linking the ligand and the transition metal to each other, and having a chemical structure in which a substituent is easily introduced at 9-position thereof, and is useful as a catalyst for preparing an ethylene homopolymer or a copolymer of ethylene and α-olefin having a structure in which the ligands are not cross-linked.

[Chemical Formula 1]

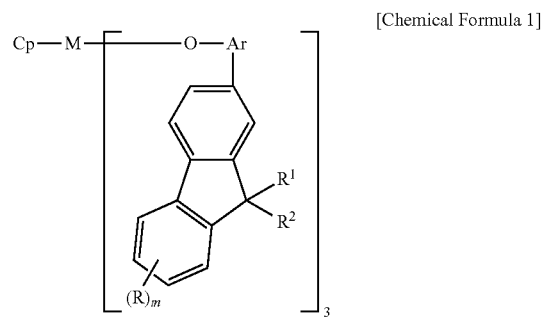

In Chemical Formula 1,

M is a Group 4 transition metal in the Periodic Table of Elements;

Cp is a cyclopentadienyl ring which is $\eta^5$-linkable to M, or a fused ring containing a cyclopentadienyl ring, the cyclopentadienyl ring or the fused ring containing a cyclopentadienyl ring is optionally substituted with one or more substituents selected from the group consisting of (C1-C20)alkyl, (C6-C30)aryl, tri(C1-C20)alkylsilyl, tri(C6-C20)arylsilyl, (C1-C20)alkyldi(C6-C20)arylsilyl, (C6-C20)aryldi(C1-C20)alkylsilyl, (C2-C20)alkenyl, and (C6-C30)aryl (C1-C20)alkyl;

Ar is (C6-C14)arylene;

$R^1$ and $R^2$ are each independently a hydrogen atom, (C1-C20)alkyl, or (C6-C30)aryl(C1-C20)alkyl;

m is an integer of 0 to 3, but when $R^1$ and $R^2$ are hydrogen atoms at the same time, m is not 0;

R is (C1-C20)alkyl, (C3-C20)cycloalkyl, (C6-C30)aryl, (C1-C20)alkyl(C6-C30)aryl, (C6-C30)aryl(C1-C20)alkyl, or (C1-C20)alkoxy, and when m is 2 or 3, the respective R(s) are the same as or different from each other; and alkyl, cycloalkyl, aryl, alkylaryl, arylalkyl, and alkoxy of R or arylene of Ar is optionally substituted with one or more substituents selected from the group consisting of halogen, (C1-C20)alkyl, (C3-C20)cycloalkyl, (C6-C30)aryl, (C6-C30)aryl(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylphosphine, (C6-C30)arylphosphine, (C1-C20)alkylmercapto, and (C6-C30)arylmercapto, or each of them is linked to an adjacent substituent via (C3-C15)alkylene or (C3-C15)alkenylene with or without a fused ring to form an alicyclic ring and a monocyclic or polycyclic aromatic ring.

In another general aspect, a catalyst composition for preparing an ethylene homopolymer or a copolymer of ethylene and α-olefin contains the transition metal compound as described above; and a cocatalyst selected from an aluminum compound a boron compound, and a mixture thereof.

In another aspect of the present invention, there is provided a method for preparing an ethylene homopolymer or a copolymer of ethylene and α-olefin using the catalyst composition as described above.

In another aspect of the present invention, there is provided an ethylene homopolymer or a copolymer of ethylene and α-olefin prepared using the transition metal compound or the catalyst composition as described above.

Advantageous Effects

A transition metal compound according to the present invention or a catalyst composition containing the transition metal compound may be economically and easily prepared by a simple synthesis process. In addition, due to excellent thermal stability of a catalyst, high catalytic activity may be maintained even at a high temperature, copolymerization reactivity with other olefins may be excellent, and a high-molecular weight polymer may be prepared with high yield. Therefore, the catalyst has higher commercial practicality than conventional metallocene and non-metallocene type single-site catalysts already known in the art. The transition metal compound according to the present invention, which has a structure in which other ligands except for a cyclopentadienyl ligand are entirely substituted with an arylene-oxide ligand, does not contain a halide ion ligand serving as a process corrosion material or an alkyl anion ligand easily modified by air at all, such that a single-site catalyst having a high activity for olefin polymerization in a commercial point of view, which is a catalyst capable of increasing economical efficiency with respect to a process investment cost, being easily prepared, being relatively stable, and having a high purity, and an ethylene homopolymer or a copolymer of ethylene and α-olefin, having various physical properties using this catalyst component may be economically prepared. Therefore, the transition metal compound according to the present invention and the catalyst composition containing the same may be usefully used to prepare the ethylene homopolymer or the copolymer of ethylene and α-olefin, having various physical properties.

BEST MODE

Hereinafter, the present invention will be described in more detail.

A transition metal compound according to an exemplary embodiment of the present invention, as represented by the following Table 1, contains a cyclopentadiene derivative around a Group 4 transition metal; and three aryloxide ligands having a fluorenyl group or a derivative thereof as a substituent at an ortho-position of an oxygen atom linking the ligand and the transition metal to each other, the fluorenyl group functioning as an electron donor, serving to further stabilize a catalyst system by surrounding the oxygen atom linking the ligand and the transition metal to each other, and having a chemical structure in which a substituent is easily introduced at 9-position thereof, and has a structure in which the ligands are not cross-linked.

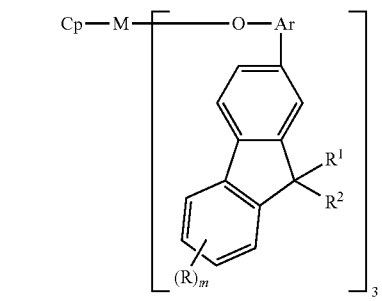

[Chemical Formula 1]

In Chemical Formula 1, M is a Group 4 transition metal in the Periodic Table of Elements;

Cp is a cyclopentadienyl ring, which is $\eta^5$-linkable to M, or a fused ring containing a cyclopentadienyl ring, the cyclopentadienyl ring or the fused ring containing a cyclopentadienyl ring is optionally substituted with one or more substituents selected from the group consisting of (C1-C20)alkyl, (C6-C30)aryl, tri(C1-C20)alkylsilyl, tri(C6-C20)arylsilyl, (C1-C20)alkyldi(C6-C20)arylsilyl, (C6-C20)aryldi(C1-C20)alkylsilyl, (C2-C20)alkenyl, and (C6-C30)aryl(C1-C20)alkyl;

Ar is (C6-C14)arylene;

$R^1$ and $R^2$ are each independently a hydrogen atom, (C1-C20)alkyl, or (C6-C30)aryl(C1-C20)alkyl;

m is an integer of 0 to 3, but when $R^1$ and $R^2$ are hydrogen atoms at the same time, m is not 0;

R is (C1-C20)alkyl, (C3-C20)cycloalkyl, (C6-C30)aryl, (C1-C20)alkyl(C6-C30)aryl, (C6-C30)aryl(C1-C20)alkyl, or (C1-C20)alkoxy, and when m is 2 or 3, the respective R(s) are the same as or different from each other; and the alkyl, cycloalkyl, aryl, alkylaryl, arylalkyl, and alkoxy of R or arylene of Ar is optionally substituted with one or more substituents selected from the group consisting of halogen, (C1-C20)alkyl, (C3-C20)cycloalkyl, (C6-C30)aryl, (C6-C30)aryl(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylphosphine, (C6-C30)arylphosphine, (C1-C20)alkylmercapto, and (C6-C30)arylmercapto, or each of them is linked to an adjacent substituent via (C3-C15)alkylene or (C3-C15)alkenylene with or without a fused ring to form an alicyclic ring and a monocyclic or polycyclic aromatic ring.

As the transition metal M in Chemical Formula 1, any Group 4 transition metal in the Periodic Table of Elements may be used, but preferably, the transition metal M is titanium (Ti), zirconium (Zr) or hafnium (Hf).

As used herein, the term "alkyl" includes both linear or branched alkyls.

As used herein, the term "aryl", an organic radical derived from aromatic hydrocarbon by the removal of one hydrogen atom, includes a single ring system or a fused ring system. Specific examples of aryl include phenyl, naphthyl, biphenyl, anthryl, fluorenyl, phenanthryl, triphenylenyl, pyrenyl, perylenyl, chrysenyl, naphtacenyl, fluoranthenyl, and the like, but are not limited thereto.

In addition, Cp is a cyclopentadiene ring, which is $\eta^5$-linkable to a core metal, a substituted cyclopentadiene ring, or a fused ring containing the cyclopentadiene ring, such as indenyl, fluorenyl, or the like, or a substituted fused ring. As used herein, the term "substituted" means that the cyclopentadienyl ring or the fused ring may be further substituted with one or more selected from the group consisting of (C1-C20)alkyl, (C6-C30)aryl, tri(C1-C20)alkylsilyl, tri(C6-C20)arylsilyl, (C1-C20)alkyldi(C6-C20)arylsilyl, (C6-C20)aryldi(C1-C20)alkylsilyl, (C2-C20)alkenyl, or (C6-C30)aryl(C1-C20)alkyl. More specifically, examples of Cp include cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, isopropylfluorenyl, and the like.

Ar is a (C6-C14)arylene, for example, phenylene, naphthalen-1-yl, naphthalen-2-yl, fluoren-2-yl, and fluoren-4-yl, and among them, phenylene and naphthalen-2-yl are preferable.

R(s) are each independently linear or branched (C1-C20) alkyl, more preferably, linear or branched (C1-C10)alkyl, for example, methyl, ethyl, n-propyl, isopropyl, n-butyl, sec-butyl, tert-butyl, n-pentyl, neopentyl, tert-pentyl, n-hexyl, n-octyl, tert-octyl, n-decyl, n-dodecyl, n-tetradecyl, n-hexadecyl, n-pentadecyl, n-octadecyl, or n-eicosyl, among them, methyl, ethyl, n-propyl, isopropyl, n-butyl, tert-butyl, or tert-octyl being preferable; (C3-C20)cycloalkyl, more preferably (C3-C10)cycloalkyl, for example, cyclopropyl, cyclobutyl, cyclopentyl, cyclohexyl, cycloheptyl, cyclooctyl, cyclodecyl, or cyclododecyl, among them, cyclohexyl being preferable; (C6-C30)aryl or (C1-C20)alkyl(C6-C30) aryl, more preferably (C6-C13)aryl or (C1-C10)alkyl(C6-C13)aryl, for example, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, naphthyl, fluorenyl, triphenyl, or anthracenyl, among them, phenyl, naphthyl, biphenyl, 2-isopropylphenyl, 3,5-xylyl, or 2,4,6-trimethylphenyl being preferable; (C6-C30)aryl(C1-C20)alkyl, more preferably (C6-C13)aryl(C1-C10)alkyl, for example, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl) methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl) methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, triphenylmethyl, naphthylmethyl, or anthracenylmethyl, among them, benzyl or triphenylmethyl being preferable; or (C1-C20)alkoxy, more preferably (C1-C10)alkoxy, for example, methoxy, ethoxy, n-propoxy, isopropoxy, n-butoxy, sec-butoxy, tert-butoxy, n-pentoxy, neopentoxy, n-hexoxy, n-octoxy, n-dodecyloxy, n-pentadecyloxy, or n-eicosyloxy, among them, methoxy or ethoxy being preferable.

In addition, m is an integer of 0 to 3, and when m is 2 or 3, the respective R(s) may be the same as or different from each other.

$R^1$ and $R^2$ substituted at the fluorenyl group of the ligand are each independently a hydrogen atom; linear or branched (C1-C20)alkyl, more preferably, linear or branched (C1-C10)alkyl, for example, methyl, ethyl, n-propyl, isopropyl, n-butyl, isobutyl, n-pentyl, n-hexyl, n-octyl, 2-ethylhexyl, n-decyl, n-dodecyl, n-tetradecyl, n-hexadecyl, n-pentadecyl, n-octadecyl, or n-eicosyl, among them, methyl, ethyl, n-propyl, isopropyl, n-butyl, isobutyl, n-pentyl, n-hexyl, or n-octyl being preferable; or (C6-C30)aryl(C1-C20)alkyl, more preferably (C6-C13)aryl(C1-C10)alkyl, for example, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl) methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl) methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-tetradecylphenyl)methyl, triphenylmethyl, naphthylmethyl, or anthracenylmethyl, among them, benzyl being preferable.

Alkyl, cycloalkyl, aryl, alkylaryl, arylalkyl, and alkoxy of R or arylene of Ar is optionally substituted with one or more substituents selected from the group consisting of halogen, (C1-C20)alkyl, (C3-C20)cycloalkyl, (C6-C30)aryl, (C6-C30)aryl(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylphosphine, (C6-C30)arylphosphine, (C1-C20)alkylmercapto, and (C6-C30) arylmercapto, wherein an example of the halogen atom may include a fluorine, chlorine, bromine, or iodine atom; an example of (C1-C20)alkyl may include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl, or n-eicosyl, among them, methyl, ethyl, isopropyl, tert-butyl, or amyl being preferable; an example of (C3-C20)cycloalkyl may include cyclopropane, cyclobutyl, cyclopentyl, cyclohexyl, cycloheptyl, or adamantyl; an example of (C6-C30)aryl or (C6-C30)aryl(C1-C20)alkyl may include phenyl, naphthyl, fluorenyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl) methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl) methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, (n-tetradecylphenyl)methyl, naphthylmethyl, or anthracenylmethyl, among them, benzyl being preferable; an example of (C1-C20)alkoxy may include methoxy, ethoxy, n-propoxy, isopropoxy, n-butoxy, sec-butoxy, tert-butoxy, n-pentoxy, neopentoxy, n-hexoxy, n-octoxy, n-dodecyloxy, n-pentadecyloxy, or n-eicosyloxy, among them, methoxy, ethoxy, isopropoxy, or tert-butoxy being preferable; an example of (C6-C30)aryloxy may include phenoxy, naphthalen-1-yloxy, naphthalen-2-yloxy, fluoren-2-yloxy, and fluoren-4-yloxy, among them, phenoxy and fluoren-2-yloxy being preferable; an example of (C3-C20)alkylsiloxy may include trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy, or tricyclohexylsiloxy, among them, trimethylsiloxy or tert-butyldimethylsiloxy being preferable; an example of (C6-C30)arylsiloxy may include triphenylsiloxy or trinaphthylsiloxy, among them, triphenylsiloxy being preferable; an example of (C1-C20) alkyl-substituted or (C6-C30)aryl-substituted amino may include dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, or methylethylamino; an example of (C1-C20) alkyl-substituted or (C6-C30)aryl-substituted phosphine may include dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, or methylethylphosphine, among them, dimethylphosphine, diethylphosphine, or diphenylphosphine being preferable; and an example of (C1-C20)alkyl-substituted or (C6-C30)aryl-substituted mercapto may include methylmercapto, ethylmercapto, propylmercapto, isopropylmercapto, 1-butylmercapto, isopentylmercapto, phenylmercapto, naphthylmercapto, or biphenylmercapto, among them, ethylmercapto or isopropylmercapto being preferable.

In addition, an example of (C3-C15)alkylene with or without a fused ring with a substituent adjacent to each of the substituents may include propylene, butylene, pentylene, hexylene, octylene, decylene, dodecylene, or pentadecylene, among them, butylene being preferable; and an example of (C3-C15)alkenylene may include prophenylene, butenylene, pentenylene, hexenylene, octenylene, decenylene, dodecenylene, or pentadecenylene, among them, prophenylene or butenylene being preferable.

More preferably, the transition metal compound represented by Chemical Formula 1 may be represented by the following Chemical Formula 2.

[Chemical Formula 2]

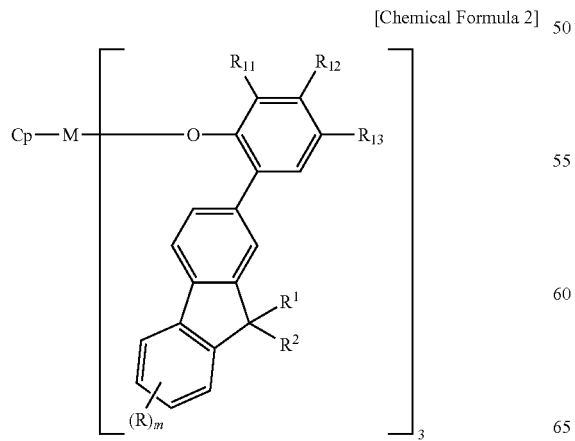

In Chemical Formula 2, M, Cp, and m are the same as defined in Chemical Formula 1;

$R^1$ and $R^2$ are each independently a hydrogen atom, (C1-C10)alkyl, or (C6-C13)aryl(C1-C10)alkyl;

R is (C1-C10)alkyl, (C3-C10)cycloalkyl, (C6-C13)aryl, (C1-C10)alkyl(C6-C13)aryl, (C6-C13)aryl(C1-C10)alkyl, or (C1-C10)alkoxy;

$R^{11}$ to $R^{13}$ are each independently hydrogen, halogen, (C1-C20)alkyl, (C3-C20)cycloalkyl, (C6-C30)aryl, (C6-C30)aryl(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylphosphine, (C6-C30)arylphosphine, (C1-C20)alkylmercapto, or (C6-C30) arylmercapto;

alkyl, cycloalkyl, aryl, alkylaryl, arylalkyl, or alkoxy of R is optionally substituted with one or more substituents selected from the group consisting of halogen, (C1-C20) alkyl, (C3-C20)cycloalkyl, (C6-C30)aryl, (C6-C30)aryl(C1-C20)alkyl, (C1-C20)alkoxy, (C6-C30)aryloxy, (C3-C20) alkylsiloxy, (C6-C30)arylsiloxy, (C1-C20)alkylamino, (C6-C30)arylamino, (C1-C20)alkylphosphine, (C6-C30) arylphosphine, (C1-C20)alkylmercapto, and (C6-C30) arylmercapto, or each of them is linked to an adjacent substituent via (C3-C15)alkylene or (C3-C15)alkenylene with or without a fused ring to form an alicyclic ring and a monocyclic or polycyclic aromatic ring.

More preferably, $R^1$ and $R^2$ substituted at the fluorenyl group of the ligand are each independently linear or branched (C1-C10)alkyl or (C6-C13)aryl(C1-C10)alkyl.

The transition metal compound represented by Chemical Formula 1 may be selected from compounds having the following structures, but is not limited thereto:

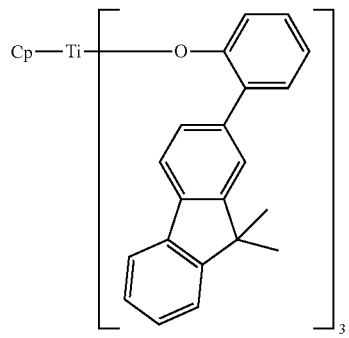

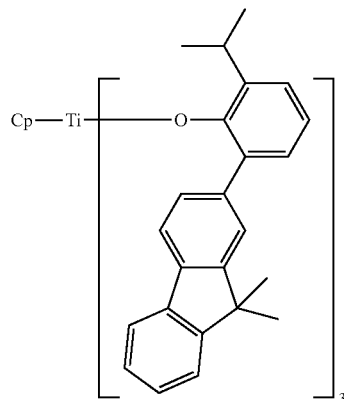

-continued
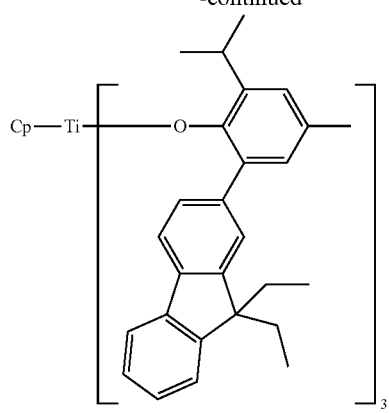
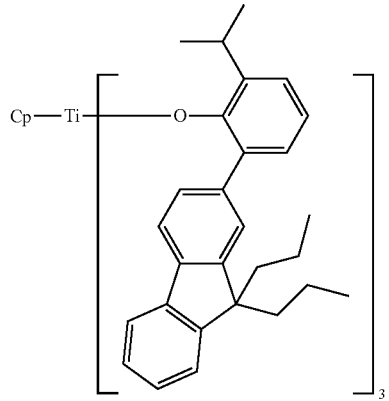
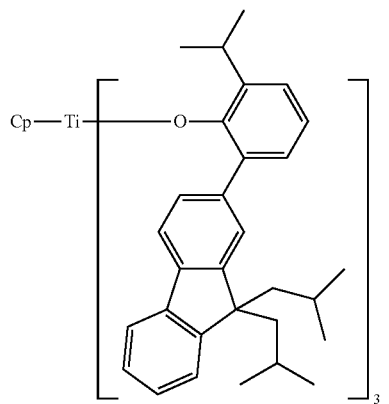
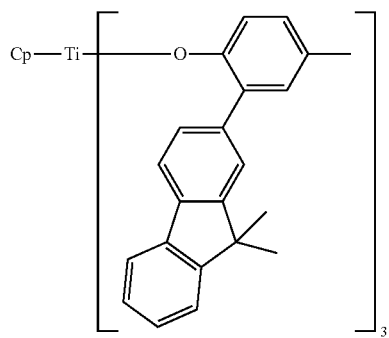
-continued
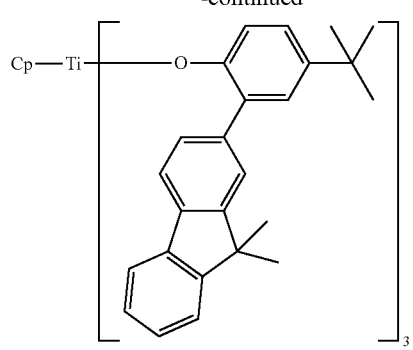
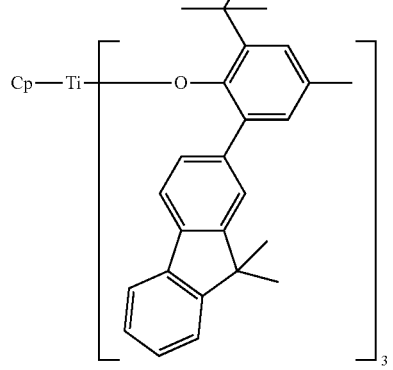
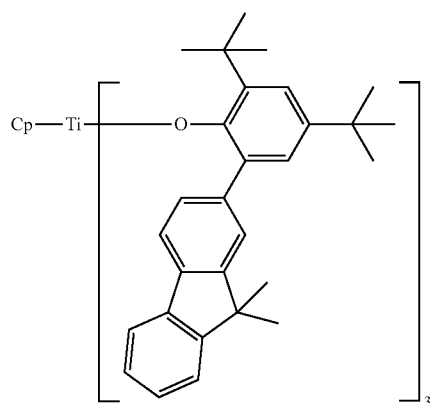
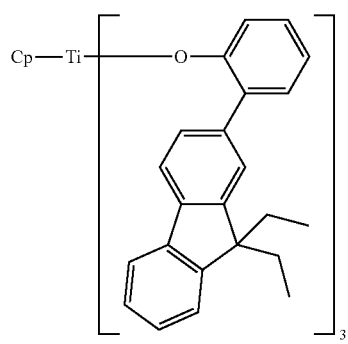

-continued
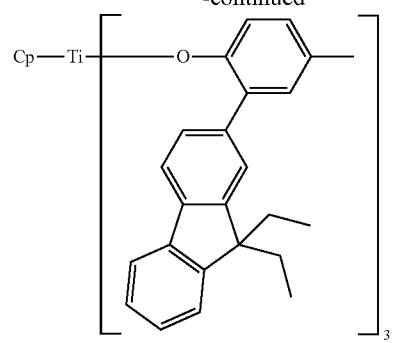
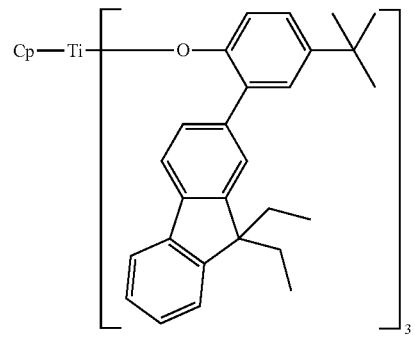
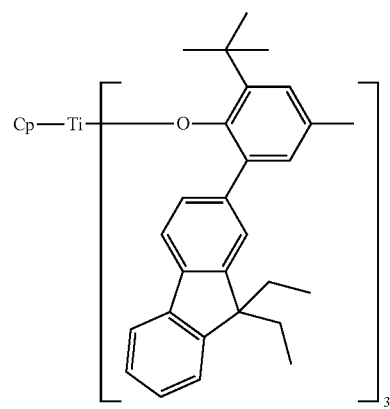
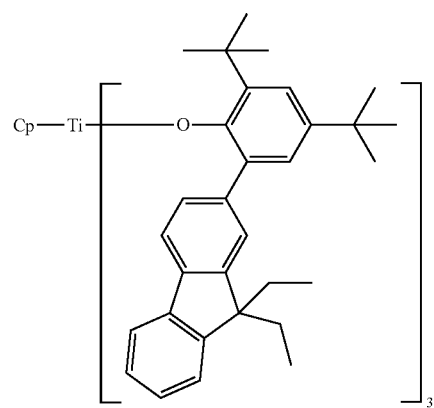
-continued
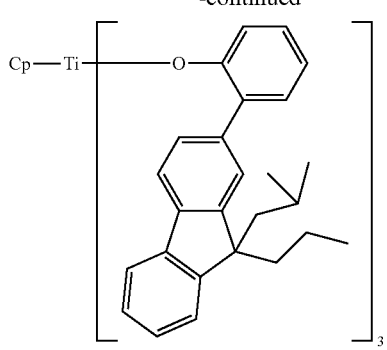
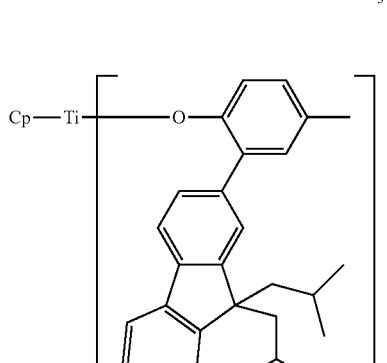
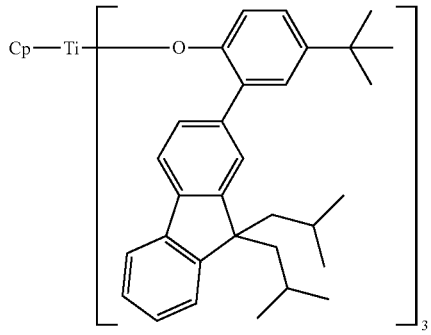
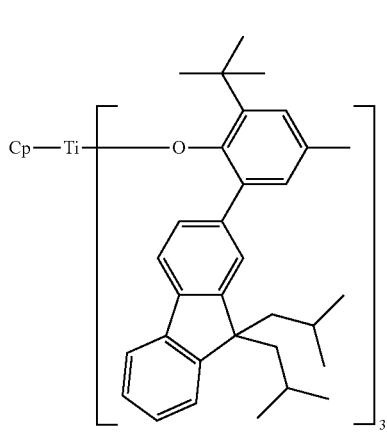

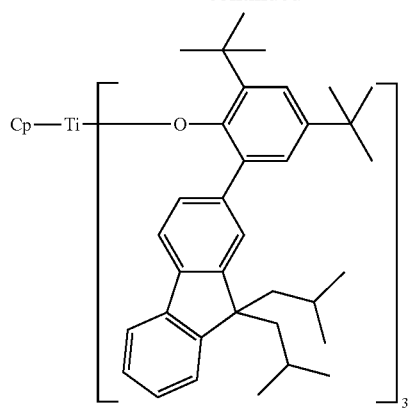
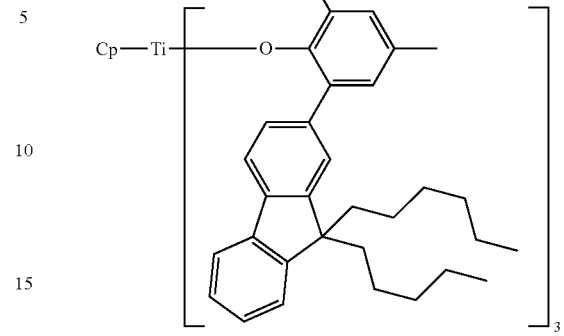
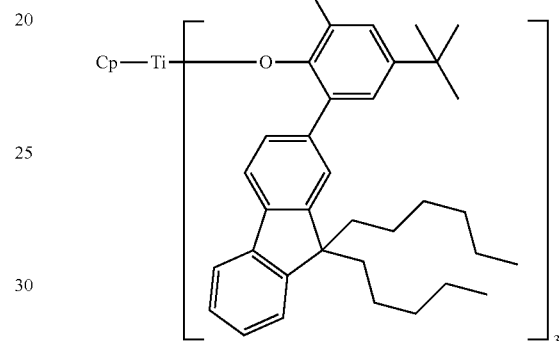
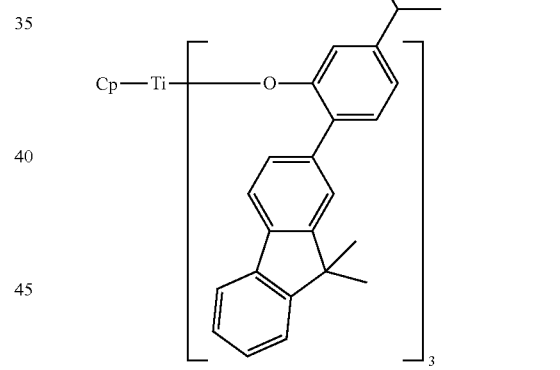
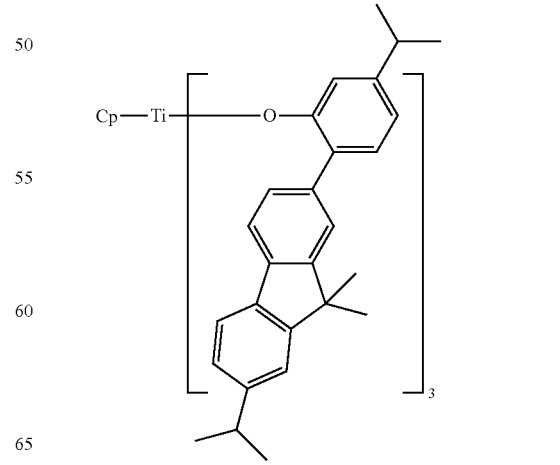

-continued
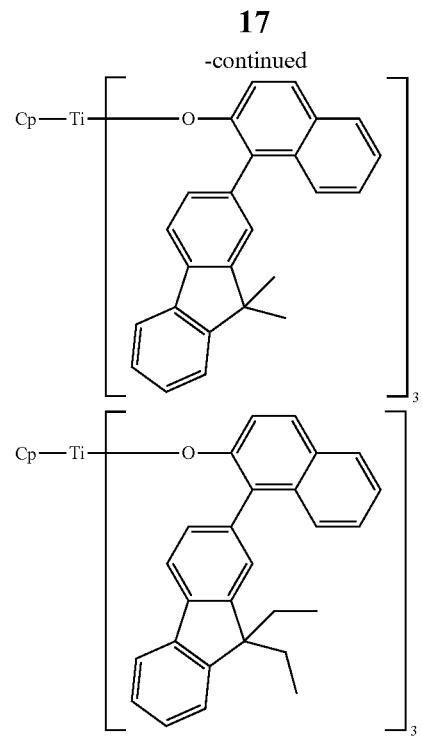
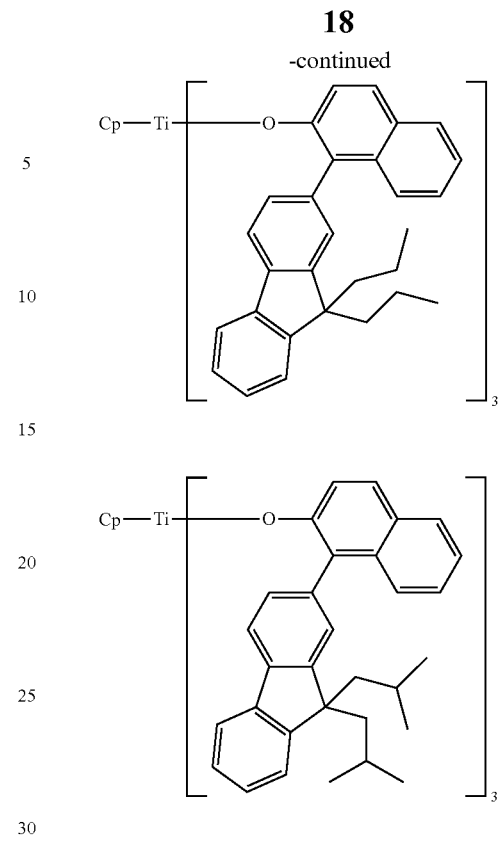
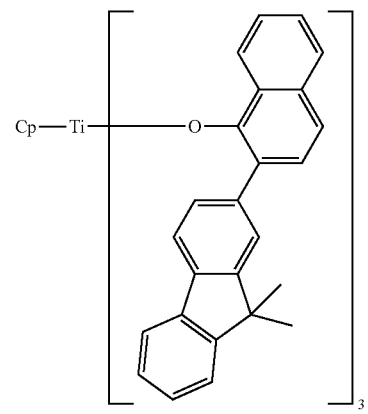
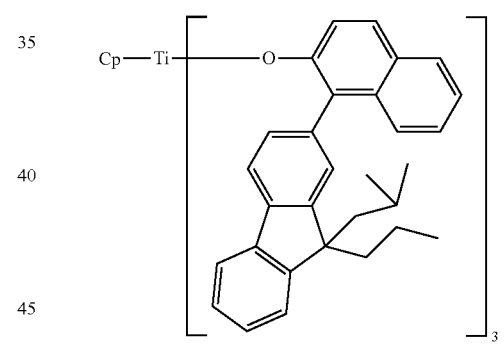
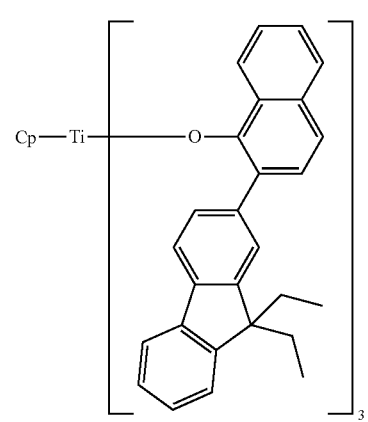
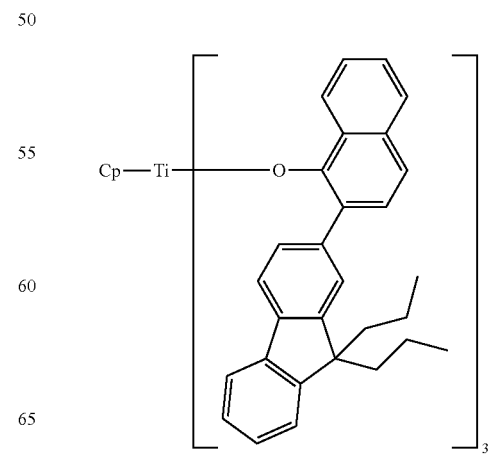

-continued

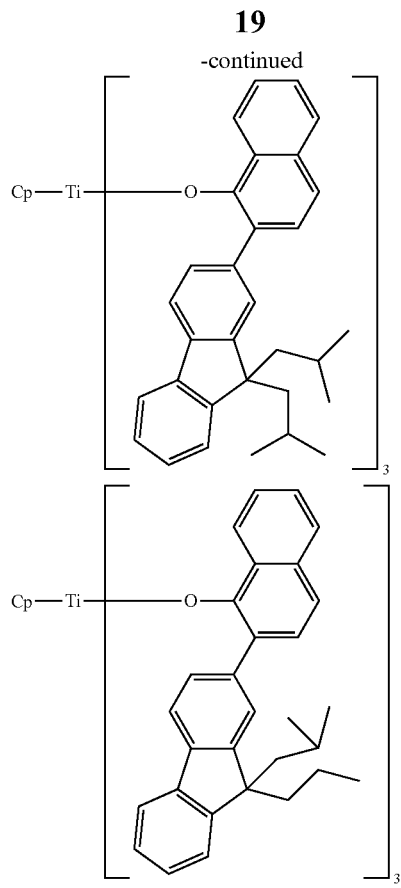

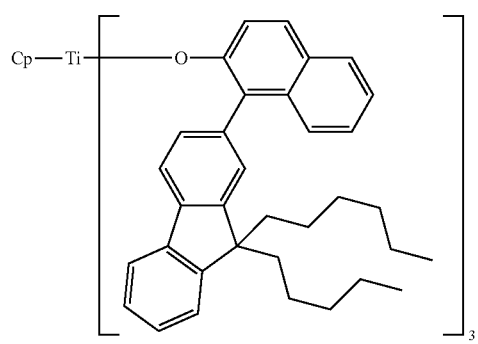

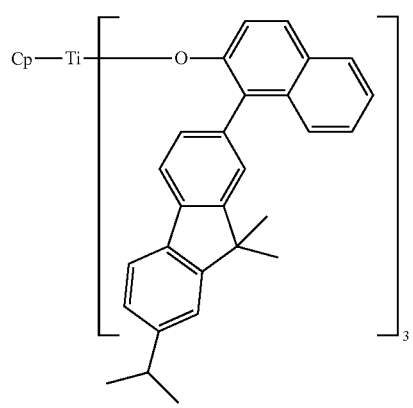

-continued

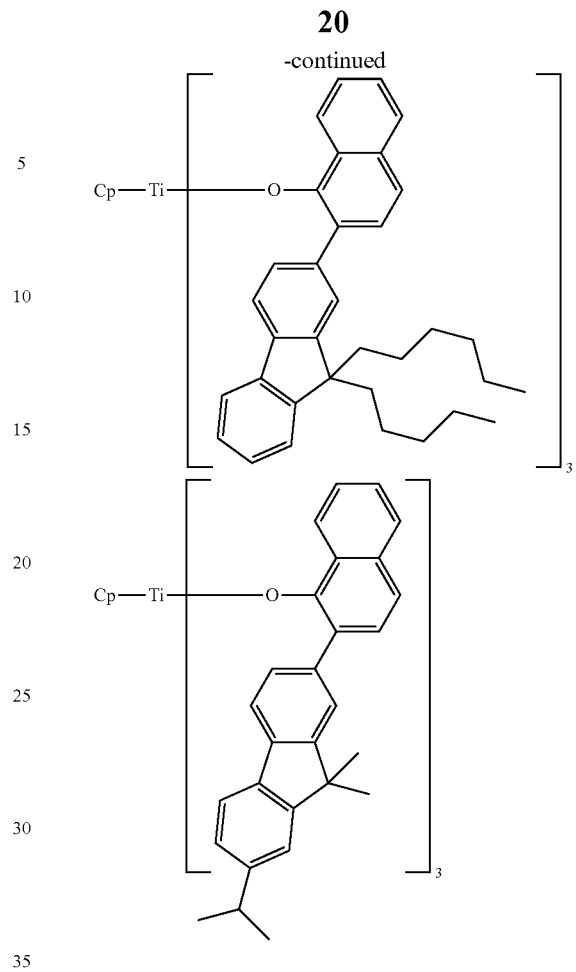

wherein, Cp is cyclopentadienyl or pentamethylcyclopentadienyl.

Meanwhile, in order to provide an active catalyst component to be used for preparing an ethylene homopolymer or a copolymer of ethylene and α-olefin, the transition metal compound represented by Chemical Formula 1 may be used preferably with an aluminum compound or boron compound which may extract a ligand from a transition metal complex to cationize the core metal and act as a counter ion, that is, an anion, having weak bond strength, or a mixture thereof as a cocatalyst. The catalyst composition containing the transition metal compound and the cocatalyst as described above may also be included in the scope of the present invention.

An example of the boron compound capable of being used as the cocatalyst in the present invention may include boron compounds disclosed in U.S. Pat. No. 5,198,401. More specifically, the boron compound may be selected from compounds represented by the following Chemical Formulas 3 to 5.

$B(R^5)_3$ [Chemical Formula 3]

$[R^6]^+[B(R^5)_4]^-$ [Chemical Formula 4]

$[(R^7)_pZH]^+[B(R^5)_4]$ [Chemical Formula 5]

In Chemical Formulas 3 to 5, B is a boron atom;

$R^5$ is a phenyl group, the phenyl group may be further substituted with three to five substituents selected from a fluorine atom, (C1-C20)alkyl substituted or unsubstituted with fluorine substituent(s), and (C1-C20)alkoxy substituted or unsubstituted with fluorine substituent(s); $R^6$ is (C5-C7) aromatic radical or (C1-C20)alkyl(C6-C20)aryl radical, (C6-C30)aryl(C1-C20)alkyl radical, for example, a triphenylmethylium radical; Z is a nitrogen or phosphorus atom; $R^7$ is (C1-C20)alkyl radical or anilinium radical substituted with two (C1-C10)alkyl groups together with a nitrogen atom; and p is an integer of 2 or 3.

A preferable example of the boron based cocatalyst may include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, triphenylmethylium tetrakis(pentafluorophenyl)borate, triphenylmethylium tetrakis(2,3,5,6-tetrafluorophenyl)borate, triphenylmethylium tetrakis(2,3,4,5-tetrafluorophenyl)borate, triphenylmethylium tetrakis(3,4,5-trifluorophenyl)borate, triphenylmethylium tetrakis(2,2,4-trifluorophenyl)borate, triphenylmethylium phenylbis(pentafluorophenyl)borate, or triphenylmethylium tetrakis(3,5-bistrifluoromethylphenyl)borate. In addition, certain compounded examples thereof include ferrocenium tetrakis(pentafluorophenyl)borate, 1,1'-dimethylferrocenium tetrakis(pentafluorophenyl)borate, tetrakis(pentafluorophenyl)borate, triphenylmethylium tetrakis(pentafluorophenyl)borate, triphenylmethylium tetrakis(3,5-bistrifluoromethylphenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, or tri(dimethylphenyl)phosphonium tetrakis(pentafluorophenyl)borate. Among them, N,N-dimethylanilinium tetrakis(pentafluorophenyl)borate, triphenylmethylium tetrakis(pentafluorophenyl)borate, or tris(pentafluoro)borane is most preferable.

An example of the aluminum compound capable of being used as the cocatalyst in the catalyst composition according to the exemplary embodiment in the present invention may include an aluminoxane compound represented by Chemical Formula 6 or 7, an organic aluminum compound represented by Chemical Formula 8, or an organic aluminum alkyloxide compound or organic aluminum aryloxide compound represented by Chemical Formula 9 or 10.

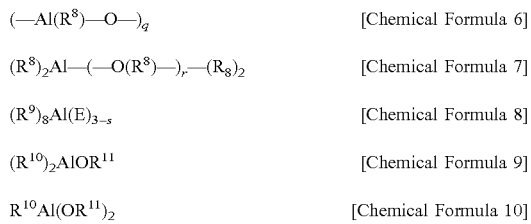

In Chemical Formulas, $R^8$ is (C1-C20)alkyl, preferably, methyl or isobutyl, q and r are each independently an integer of 5 to 20; $R^9$ and $R^{10}$ are each independently (C1-C20)alkyl; E is a hydrogen atom, a halogen atom, or (C1-C20)alkyl; s is an integer of 1 to 3; and $R^{11}$ is (C1-C20)alkyl or (C6-C30)aryl.

Specific examples of the aluminum compound may include aluminoxane compounds, such as methylaluminoxane, modified methylaluminoxane, tetraisobutylaluminoxane; organic aluminum compounds, such as trialkylaluminum including trimethylaluminum, triethylaluminum, tripropylaluminum, triisobutylaluminum, trihexylaluminum, and trioctylaluminum; dialkylaluminum chloride including dimethylaluminum chloride, diethylaluminum chloride, dipropylaluminum chloride, diisobutylaluminum chloride, and dihexylaluminum chloride; alkylaluminum dichloride including methylaluminum dichloride, ethylaluminum dichloride, propylaluminum dichloride, isobutylaluminum dichloride and hexylaluminum dichloride; and dialkylaluminum hydride including dimethylaluminum hydride, diethylaluminum hydride, dipropylaluminum hydride, diisobutylaluminum hydride and dihexylaluminum hydride. The aluminum compound is preferably the aluminoxane compound, trialkylaluminum or a mixture thereof, and more preferably, methylaluminoxane, modified methylaluminoxane, triethylaluminum, triisobutylaluminum, or a mixture thereof.

In the case in which the aluminum compound is used as a cocatalyst in a transition metal catalyst composition for preparing an ethylene homopolymer or a copolymer of ethylene and α-olefin containing the cocatalyst according to the present invention, a ratio of the transition metal M in Chemical Formula 1: an aluminum (Al) atom is 1:10 to 5,000 on the basis of a molar ratio thereof. Further, in the transition metal catalyst composition for preparing an ethylene homopolymer or a copolymer of ethylene and α-olefin containing the cocatalyst according to the present invention, a ratio of the transition metal compound represented by Chemical Formula 1 and the cocatalyst is in a range of preferably 1:0.1 to 200:10 to 1,000, and more preferably, 1:0.5 to 5:25 to 500 on the basis of a molar ratio of the core metal M:a boron (B) atom:aluminum (Al) atom. The above ratio enables the preparation of the ethylene homopolymers or the copolymers of ethylene and α-olefin, and the range of the ratio may be varied depending on purity of reaction.

In another aspect of the present invention, the method for preparing ethylene based polymers by using the transition metal catalyst composition may be carried out by contacting the transition metal catalyst, the cocatalyst, and ethylene, or α-olefin comonomers as needed, in the presence of a suitable organic solvent. Here, the transition metal catalyst and the cocatalyst components may be separately fed to the reactor, or those components may be mixed in advance and then fed to the reactor. The mixing conditions, such as the order of feeding, temperature, or concentration, are not particularly restricted.

Preferable examples of organic solvents usable in the preparing method may include (C3-C20) hydrocarbon, and specific examples thereof may include butane, isobutane, pentane, hexane, heptane, octane, isooctane, nonane, decane, dodecane, cyclohexane, methylcyclohexane, benzene, toluene, xylene, and the like.

Specifically, ethylene may be used alone as the monomer, in the preparation of the ethylene homopolymer. Here, the suitable pressure of ethylene may be 1 to 1000 atm, more preferably, 1 to 150 atm. In addition, it is effective that an internal temperature of a reactor for a polymerization reaction is in a range of 60° C. to 300° C., preferably, 80° C. to 250° C., and more preferably, 130° C. to 220° C.

Further, in the case of preparing the copolymer of ethylene and α-olefin, (C3-C18) α-olefin may be used as a comonomer together with ethylene. Preferably, the α-olefin may be selected from the group consisting of propylene, 1-butene, 1-pentene, 4-methyl-1-pentene, 1-hexene, 1-octene, 1-decene, 1-dodecene, 1-hexadecene, and 1-octadecene. More preferably, 1-butene, 1-hexene, 1-octene, or 1-decene and ethylene may be copolymerized. Here, preferable ethylene pressure and polymerization reaction temperature are the same as the case where ethylene homopolymers are prepared. The copolymer prepared according to the method of the present invention may contain ethylene in a content of 50 wt % or more, preferably 60 wt % or more, and more preferably 60 to 99 wt %.

As described above, a linear low density polyethylene (LLDPE) prepared by using (C3-C18) α-olefin as the comonomer has a density range from 0.910 to 0.940 g/cc, and may be extended up to a region of ultra low density polyethylene (VLDPE or ULDPE) or an olefin elastomer, which has a density of 0.910 g/cc or less. In addition, when the ethylene homopolymer or copolymer according to the present invention is prepared, hydrogen may be used as a molecular weight regulator in order to regulate the molecular weight. The weight average molecular weight (Mw) thereof is generally in the range of 80,000 to 5000,000 g/mol.

Since the catalyst composition suggested in the present invention exists in a homogeneous state in a polymerization reactor, it is preferable that the catalyst composition is applied to a solution polymerization process performed at a temperature higher than a melting point of the corresponding polymer. However, as disclosed in U.S. Pat. No. 4,752,597, the transition metal catalyst and the cocatalyst may be supported on a porous metal oxide supporter to thereby be used in a form of a heterogeneous catalyst composition in a slurry polymerization process or vapor phase polymerization process.

Hereinafter, the present invention will be described in detail through Examples, but the scope of the present invention is not limited thereto.

Unless mentioned otherwise, all experiments for synthesizing ligands and catalysts were carried out under nitrogen atmosphere by using standard Schlenk or glove-box techniques. The organic solvents used in the reaction were subjected to reflux over sodium metal and benzophenone to thereby remove moisture, and then distilled immediately before use. $^1$H-NMR analysis of the synthesized ligands and catalysts were performed by using Bruker 500 MHz at room temperature.

Cyclohexane corresponding to a polymerization solvent was used after passing through a tube filled with molecular sieve 5 Å and activated alumina, and being bubbled by high-purity nitrogen to sufficiently remove moisture, oxygen and other catalyst poison materials. Polymerized polymers were analyzed by the measurement methods described below.

1. Melt Flow Index (MI)
MI was measured according to ASTM D2839.
2. Density
Density was measured by using a density gradient tube, according to ASTM D 1505.

EXAMPLE 1

Synthesis of tris(2-(9',9"-dimethylfluoren-2'-yl)phenoxy)(pentamethylcyclopentadienyl)titanium (IV)

1) Synthesis of 2-bromo-9,9'-dimethylfluorene 2-bromofluorene (25 g, 102.0 mmol), iodomethane (43.4 g, 306.0 mmol), and dimethylsulfoxide (DMSO, 300 mL) were put into a 1000 mL 3-neck round flask, and dissolved by stirring under nitrogen atmosphere. Potassium-tert-butoxide (32.1 g, 285.6 mmol) were dissolved in DMSO (400 mL) and then added dropwise thereto. After the mixture was stirred at room temperature for 12 hours and then stirred again at 80° C. for 1 hour, a temperature of the mixture was lowered to room temperature. The mixture was mixed with water (1000 mL), and then extracted with normal-hexane (n-hexane). An organic mixture was washed three times with distilled water, dried over anhydrous magnesium sulfate (MgSO$_4$), and evaporated using a rotary evaporator to remove the solvent. The resultant was purified with n-hexane using a silica gel chromatography tube, and recrystallized again in n-hexane, thereby obtaining 2-bromo-9,9'-dimethylfluorene (27.0 g, yield: 96.9%) as a white solid.

$^1$H-NMR (CDCl$_3$) δ=1.65(s, 6H), 7.35-7.39(m, 2H), 7.44-7.50(m, 2H), 7.58-7.62(m, 2H), 7.72-7.73(m, 1H) ppm 2) Synthesis of 2-(2"-methoxyphenyl)-9,9'-dimethylfluorene A mixed solution of water (70 mL) and dimethoxyethane (150 mL) was added to a flask charged with 2-bromo-9,9'-dimethylfluorene (27.0 g, 98.8 mmol), 2-methoxyphenylboronic acid (18.0 g, 118.6 mmol), palladium acetate (0.13 g, 0.6 mmol), triphenylphosphine (0.94 g, 3.6 mmol), and potassium phosphate (40.9 g, 177.9 mmol), and refluxed for 6 hours. The resultant material was cooled to room temperature, and then an ammonium chloride aqueous solution (150 mL) and diethyl ether (200 mL) were added thereto, followed by separation of the organic layer. The residue was extracted with diethyl ether, and the collected organic layer was dried over magnesium sulfate, followed by removal of volatile materials, and then purified with hexane using a silica gel chromatography tube, thereby obtaining 2-(2"-methoxyphenyl)-9,9'-dimethylfluorene (28.0 g, yield: 94.0%) as a solid.

$^1$H-NMR (CDCl$_3$) δ=1.56(s, 6H), 3.88(s, 3H), 7.04-7.06 (d, 1H), 7.08-7.11(t, 1H), 7.33-7.39(m, 3H), 7.43-7.45(d, 1H), 7.47-7.48(d, 1H), 7.56-7.58(d, 1H), 7.63(s, 1H), 7.76-7.840(t, 2H) ppm 3) Synthesis of 2-(9',9"-dimethylfluoren-2-yl)phenol After dissolving 2-(2"-methoxyphenyl)-9,9'-dimethylfluorene (25.0 g, 83.2 mmol) in methylene chloride (400 mL), boron tribromide (100 mL) (1 M in methylene chloride) was added dropwise thereto at −78° C., and a reaction was carried out for three hours while slowly raising the temperature to room temperature. After the reaction, a mixed solution of ice (150 g) and diethyl ether (300 mL) was added thereto, followed by separation of the organic layer. The aqueous layer was extracted with diethyl ether, and the collected organic layer was dried over magnesium sulfate, followed by removal of volatile materials, and then purified with a mixed solution of hexane and methylene chloride using a silica gel chromatography tube, thereby obtaining 2-(9',9"-dimethylfluoren-2'-yl)phenol (18.0 g, yield 75.75%) as a white solid.

$^1$H-NMR (CDCl$_3$) δ=1.55(s, 6H), 7.04-7.07(m, 2H), 7.30-7.40(m, 4H), 7.47-7.50(m, 2H), 7.55(s, 1H), 7.78-7.80(d, 1H), 7.85-7.87(d, 1H) ppm 4) Synthesis of tris(2-(9',9"-dimethylfluoren-2'-yl)phenoxy)(pentamethylcyclopentadienyl)titanium (IV)

After 2-(9',9"-dimethylfluoren-2'-yl)phenol (15.0 g, 51.3 mmol) was dissolved in toluene (200 mL), a temperature of the solution was lowered to −78° C., and n-butyl lithium (2.5

M in hexane, 20.7 mL) was slowly added thereto. When addition was completed, a reaction temperature was raised to room temperature, and the mixture was stirred for 12 hours, thereby carrying out a reaction. After the reaction for 12 hours, the temperature of the reaction solution was lowered again to −78° C., and (pentamethylcyclopentadienyl)titanium (IV) trichloride (4.7 g, 16.3 mmol) was dissolved in toluene (100 mL) and slowly added thereto. Then, a reaction temperature was raised to room temperature and the mixture was stirred for 12 hours, thereby carrying out a reaction. When the reaction was completed, a salt was removed by filtering, the solvent was removed from the filtrate by distillation under reduced pressure, and the resultant was recrystallized with purified toluene and hexane at −35° C. A precipitated solid was filtered and then dried under reduced pressure, thereby obtaining tris(2-(9',9"-dimethylfluoren-2'-yl)phenoxy)(pentamethylcyclopentadienyl)titanium (IV) (10.8 g, yield 63.9%) as a yellow solid component.

$^1$H-NMR ($C_6D_6$) δ=1.38(s, 15H), 1.42 (s, 18H), 6.92 (dd, 3H), 7.14 (m, 3H), 7.23 (m, 6H), 7.29 (m, 6H), 7.40 (d, 3H), 7.56 (s, 6H), 7.63 (m, 3H), 7.71 (d, 3H) ppm

COMPARATIVE PREPARATION EXAMPLE 1

Synthesis of (dichloro)(pentamethylcyclopentadienyl)(2-(9',9"-dimethylfluoren-2'-yl)phenoxy)titanium (IV)

After 2-(9',9"-dimethylfluoren-2'-yl)phenol (5.0 g, 17.1 mmol) was dissolved in toluene (100 mL), a temperature of the solution was lowered to −78° C., and n-butyl lithium (2.5 M in hexane, 6.9 mL) was slowly added thereto. When addition was completed, a reaction temperature was raised to room temperature, and the mixture was stirred for 12 hours, thereby carrying out a reaction. After the reaction for 12 hours, the temperature of the reaction solution was lowered again to −78° C., and (pentamethylcyclopentadienyl)titanium (IV) trichloride (4.7 g, 16.3 mmol) was dissolved in toluene (100 mL) and slowly added thereto. Then, a reaction temperature was raised to room temperature and the mixture was stirred for 12 hours, thereby carrying out a reaction. When the reaction was completed, a salt was removed by filtering, the solvent was removed from the filtrate by distillation under reduced pressure, and the resultant was recrystallized with purified toluene and hexane at −35° C. A precipitated solid was filtered and then dried under reduced pressure, thereby obtaining (dichloro)(pentamethylcyclopentadienyl)(2-(9',9"-dimethylfluoren-2'-yl)phenoxy)titanium (IV) (5.6 g, yield 63.9%) as a red solid component.

$^1$H-NMR ($C_6D_6$) δ=1.61(s, 6H), 1.77(s, 15H), 7.03-7.05 (t, 1H), 7.16-7.19(t, 1H), 7.32-7.34(m, 2H), 7.37-7.39(d, 1H), 7.42-7.44(d, 1H), 7.46-7.47(d, 1H), 7.71-7.77(m, 3H), 7.82-7.84(d, 1H) ppm

COMPARATIVE PREPARATION EXAMPLE 2

Synthesis of (2-(9',9"-dimethylfluoren-2'-yl)phenoxy)dimethyl(pentamethylcyclopentadienyl)titanium (IV)

(Dichloro)(pentamethylcyclopentadienyl)(2-(9',9"-dimethylfluoren-2'-yl)phenoxy)titanium (IV) (5 g, 9.3 mmol) prepared by the method in Comparative Preparation Example 1 was dissolved in toluene (100 mL), a temperature was lowered to −78° C. Methyl lithium (1.6 M in diethyl ether, 17.4 mL) was slowly added thereto at the same temperature, and when addition was completed, the temperature was raised to room temperature, and the mixture was stirred for 12 hours. When the reaction was completed, a salt was removed by filtering, the solvent was removed from the filtrate by distillation under reduced pressure, and the resultant was recrystallized with purified hexane at −35° C. At this time, a precipitated solid was filtered and then dried under reduced pressure, thereby obtaining (2-(9',9"-dimethylfluoren-2'-yl)phenoxy)dimethyl(pentamethylcyclopentadienyl)titanium (IV) (3.5 g, yield 55.8%) as a yellow solid component.

$^1$H-NMR ($C_6D_6$) δ=0.81 (s, 6H), 1.53 (s, 6H), 1.63 (s, 15H), 7.12 (m, 2H), 7.21 (m, 1H), 7.33 (m, 2H), 7.51 (d, 1H), 7.25 (m, 2H), 7.80 (d, 1H) ppm

EXAMPLES 3 AND 4 AND COMPARATIVE EXAMPLES 1 TO 4

Copolymerization of ethylene and 1-octene

Copolymerization of ethylene and 1-octene was performed as described below using a batch type polymerization apparatus.

After putting methylcyclohexane (1200 mL) and 1-octene into a 2000 mL stainless steel reactor, which had been sufficiently dried and purged with nitrogen, 54.2 mM solution (11.1 mL) of modified methylaluminoxane-7 (modified MAO-7, 7 wt % Al Isopar solution, from Akzo Nobel) in toluene was added thereto. Then, a temperature of the reactor was raised to 140° C., and 0.08 mL of each of the titanium (IV) compounds (27 mM solution in toluene) synthesized in Example 1 and Comparative Preparation Examples 1 and 2 and 0.6 mL of triphenylmethylium tetrakis (pentafluorophenyl)borate (99%, Boulder Scientific) (10 mM solution in toluene) were sequentially added thereto. By means of ethylene, the pressure in the reactor was then made up to 20 kg/cm$^2$, with continual supply thereof to carry out polymerization. After the reaction was carried out for 10 minutes, 100 mL of ethanol containing 10 vol % of aqueous hydrochloric acid solution was added to quench the polymerization. Then, the mixture was stirred with 1.5 L of ethanol for 1 hour, and the reaction product was filtered and separated. The collected reaction product was dried in a vacuum oven at 60° C. for 8 hours.

In Example 4 and Comparative Examples 3 and 4, the titanium (IV) compounds prepared in Example 1 and Comparative Preparation Examples 1 and 2 were kept in air for 24 hours, and then used as catalysts. A content of used octene, a catalytic activity, a melt flow index (MI), and density are illustrated in the following Table 1.

TABLE 1

| Kind | | Whether or not the catalyst was kept in air for 24 hours | Used Octene (mL) | Catalytic Activity (weight (Kg) of Polymer/Amount (mmol) of Used Catalyst) | MI | Density (g/cc) |
|---|---|---|---|---|---|---|
| | Catalyst | | | | | |
| Example 3 | Example 1 | X | 20 | 15.38 | 5.2 | 0.9161 |
| Example 4 | Example 1 | ○ | 20 | 15.01 | 4.6 | 0.9161 |
| Comparative Example 1 | Comparative preparation Example 1 | X | 20 | 14.73 | 9.5 | 0.9165 |
| Comparative Example 2 | Comparative preparation Example 2 | X | 20 | 15.21 | 7.8 | 0.9158 |
| Comparative Example 3 | Comparative preparation Example 1 | ○ | 20 | 14.98 | 8.1 | 0.9168 |
| Comparative Example 4 | Comparative preparation Example 2 | ○ | 20 | 10.24 | 10.3 | 0.9166 |

As seen from the Examples, in Examples 3 and 4, MI values were lower than those in Comparative Examples, such that polymers having a large weight average molecular weight may be produced even under a high temperature condition of 140° C. or more. Particularly, a high-molecular weight and low-density copolymer may be successfully obtained using ethylene and 1-octene.

EXAMPLE 5 AND COMPARATIVE EXAMPLE 5

Copolymerization of ethylene and 1-octene

Copolymerization of ethylene and 1-octene was performed as described below using a continuous polymerization apparatus.

As a single-site catalyst, each of the titanium (IV) compounds synthesized in Example 1 and Comparative Preparation Example 1 was used, and as a solvent, methylcyclohexane was used. An amount of the used catalyst was illustrated in the following Table 2. As an aluminum cocatalyst, modified methylaluminoxane-7 (modified MAO-7, 7 wt % Al Isopar solution, from Akzo Nobel) was used, and as a boron based cocatalyst, triphenylmethylium tetrakis(pentafluorophenyl)borate (99%, Boulder Scientific) was used. Each of the catalysts was injected after being dissolved in toluene at a concentration of 0.3 g/L, and polymerization was performed using 1-octene as an α-olefin comonomer. A conversion rate of the reactor was measured by gas chromatography analysis of a process stream after the reaction. In the case of the single-site catalyst, a molecular weight was controlled as a function of the reactor temperature and a content of 1-octene, and detailed polymerization conditions and polymerization results are illustrated in the following Table 2.

TABLE 2

| | Classification | Example 5 | Comparative Example 5 |
|---|---|---|---|
| Polymerization Conditions | Catalyst | Example 1 | Comparative Preparation Example 1 |
| | Flow Rate of Overall Solution (kg/h) | 5 | 5 |

TABLE 2-continued

| | Classification | Example 5 | Comparative Example 5 |
|---|---|---|---|
| | Amount of Injected ethylene (wt %) | 10 | 10 |
| | Ratio of Injected 1-octent (1-octene/ethylene) | 0.19 | 0.19 |
| | Amount of Injected Ti (μmol/kg) | 5.5 | 9.5 |
| | Al/Ti molar ratio | 30 | 30 |
| | B/Ti molar ratio | 3 | 3 |
| | Reaction Temperature (° C.) | 150.5 | 150.4 |
| Polymerization Results | Ethylene Conversion Rate (%) | 95 | 95 |
| | MI | 3.242 | 26.600 |
| | Density (g/cc) | 0.9136 | 0.9164 |

Ti means Ti in a single-site catalyst.
Al indicates an aluminum (Al) atom in modified methylaluminoxane-7 (modified MAO-7, 7 wt % Al Isopar solution, from Akzo Nobel) corresponding to the cocatalyst.
B indicates a boron (B) atom in triphenylmethylium tetrakis (pentafluorophenyl) borate.

Referring to Comparative Example 5 and Example 5 of Table 2, it may be appreciated that the amount of the injected Ti catalyst was smaller in Example 5, and thus, in Example 5, an amount of the catalyst required for achieving the same ethylene conversion rate (95%) was smaller than that in Comparative Example 5. That is, it may be appreciated that in Example 5, the catalytic activity was higher. In addition, densities of the polymers prepared in Comparative Example 5 and Example 5 were similar to each other, but in Example 5, a MI value of the polymer formed at the same reaction temperature was lower than that in Comparative Example 5. Therefore, it may be confirmed that the catalyst of Example 5 produced a polymer having a higher molecular weight at a high temperature of 150° C.

Although the exemplary embodiments of the present invention have been disclosed in detail, those skilled in the art will appreciate that various modifications are possible, without departing from the scope and spirit of the present invention as disclosed in the accompanying claims. Accordingly, such modifications of the exemplary embodiment of the present invention should also be understood to fall within the scope of the present invention.

INDUSTRIAL APPLICABILITY

A transition metal compound according to the present invention or a catalyst composition containing the transition metal compound may be economically and easily prepared by a simple synthesis process. In addition, due to excellent thermal stability of a catalyst, high catalytic activity may be maintained even at a high temperature, copolymerization reactivity with other olefins may be excellent, and a high-molecular weight polymer may be prepared with high yield. Therefore, the catalyst has higher commercial practicality than conventional metallocene and non-metallocene type single-site catalysts already known in the art. The transition metal compound according to the present invention, which has a structure in which other ligands except for a cyclopentadienyl ligand are entirely substituted with an arylene-oxide ligand, does not contain a halide ion ligand serving as a process corrosion material or an alkyl anion ligand easily modified by air at all, such that a single-site catalyst having a high activity for olefin polymerization in a commercial point of view, which is a catalyst capable of increasing economical efficiency with respect to a process investment cost, being easily prepared, being relatively stable, and having a high purity, and an ethylene homopolymer or a copolymer of ethylene and α-olefin, having various physical properties using this catalyst component may be economically prepared. Therefore, the transition metal compound according to the present invention and the catalyst composition containing the same may be usefully used to prepare the ethylene homopolymer or the copolymer of ethylene and α-olefin, having various physical properties.

The invention claimed is:

1. A transition metal compound represented by the following Chemical Formula 1:

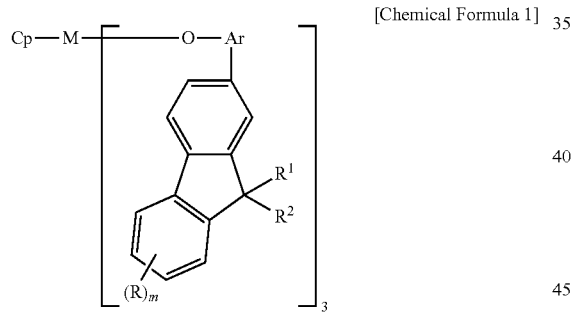

[Chemical Formula 1]

in Chemical Formula 1, M is a Group 4 transition metal in the Periodic Table of Elements;

Cp is a cyclopentadienyl ring, which is $\eta^5$ bonded to M, or a fused ring containing a cyclopentadienyl ring, the cyclopentadienyl ring or the fused ring containing a cyclopentadienyl ring is optionally substituted with one or more substituents selected from the group consisting of (C1-C20)alkyl, (C6-C30)aryl, tri(C1-C20)alkylsilyl, tri(C6-C20)arylsilyl, (C1-C20)alkyldi(C6-C20)arylsilyl, (C6-C20)aryldi(C1-C20)alkylsilyl, (C2-C20)alkenyl, and (C6-C30)aryl(C1-C20)alkyl;

Ar is (C6-C14)arylene;

$R^1$ and $R^2$ are each independently a hydrogen atom, (C1-C20)alkyl, or (C6-C30)aryl(C1-C20)alkyl;

m is an integer of 0 to 3, with the provisio when $R^1$ and $R^2$ are hydrogen atoms at the same time, m is not 0;

R is independently (C1-C20)alkyl, (C3-C20)cycloalkyl, (C6-C30)aryl, (C1-C20)alkyl(C6-C30)aryl, (C6-C30)aryl(C1-C20)alkyl, or (C1-C20)alkoxy, and when m is 2 or 3, wherein the alkyl, cycloalkyl, aryl, alkylaryl, arylalkyl, and alkoxy of R, and arylene of Ar are optionally substituted with one or more substituents selected from the group consisting of halogen, (C1-C20)alkyl, (C3-C20)cycloalkyl, (C6-C30)aryl, (C6-C30)aryl(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylphosphine, (C6-C30)arylphosphine, (C1-C20)alkylmercapto, and (C6-C30)arylmercapto, wherein adjacent R groups are optionally joined together to form an alicyclic ring and a monocyclic or polycyclic aromatic ring.

2. The transition metal compound of claim 1, wherein Ar is selected from the group consisting of phenylene, naphthalen, and fluorene.

3. The transition metal compound of claim 1, wherein M is titanium, zirconium, or hafnium.

4. The transition metal compound of claim 2 is selected from the following Compounds:

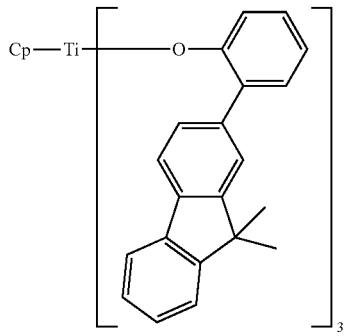

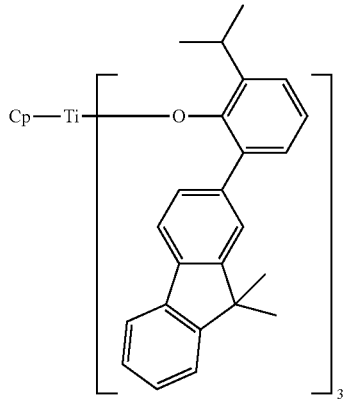

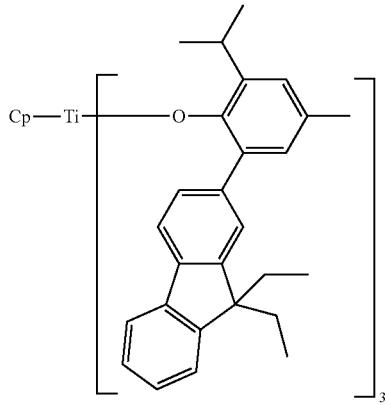

31
-continued
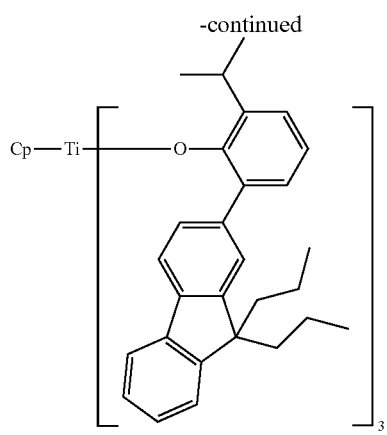
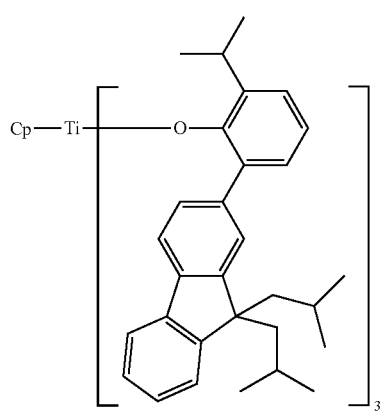
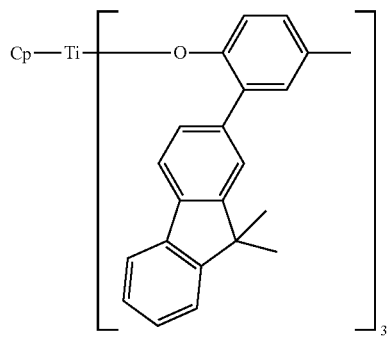
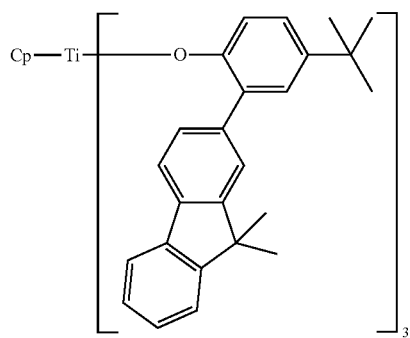
32
-continued
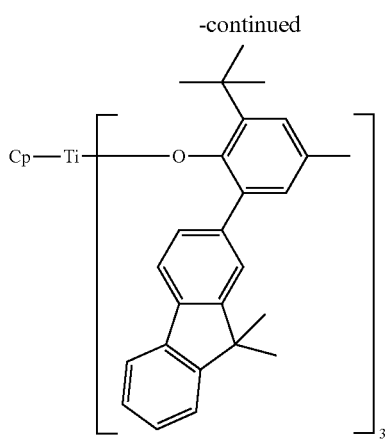
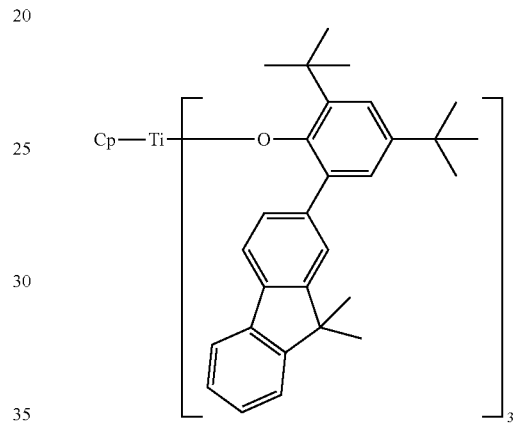
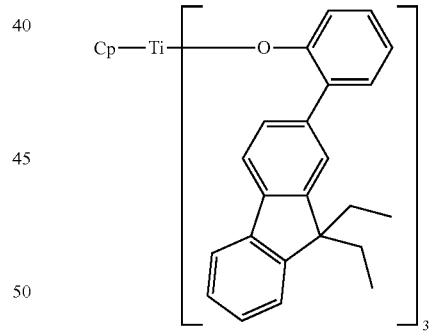
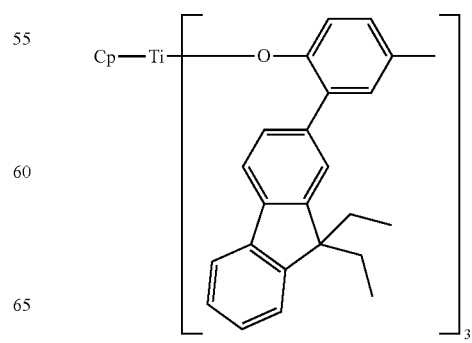

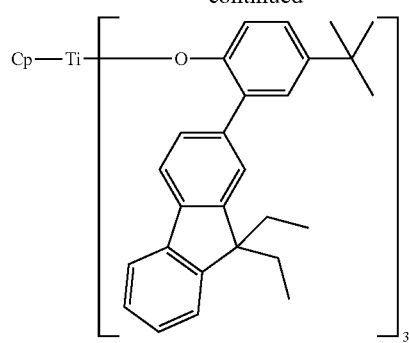
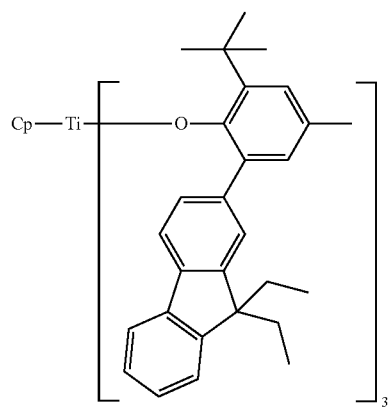
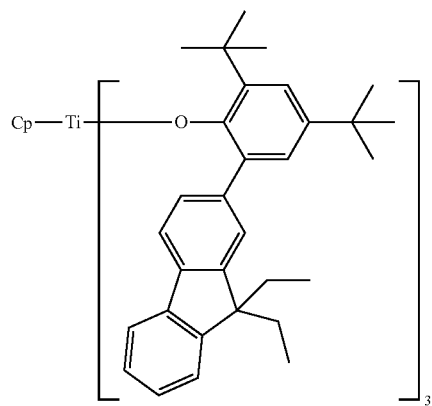
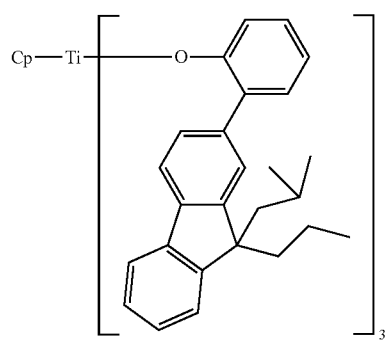
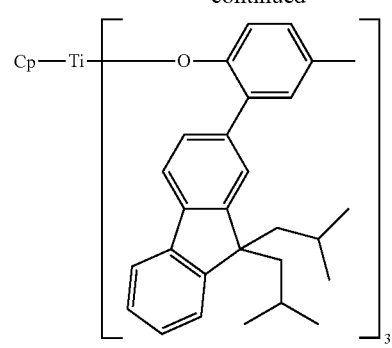
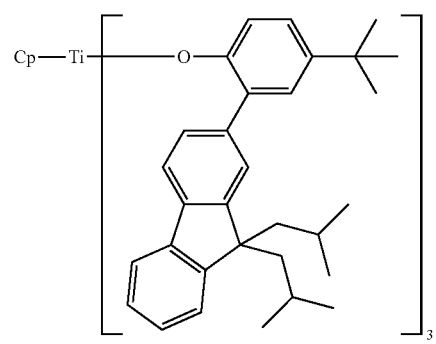
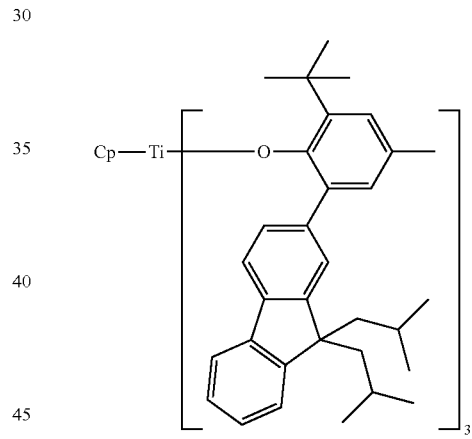
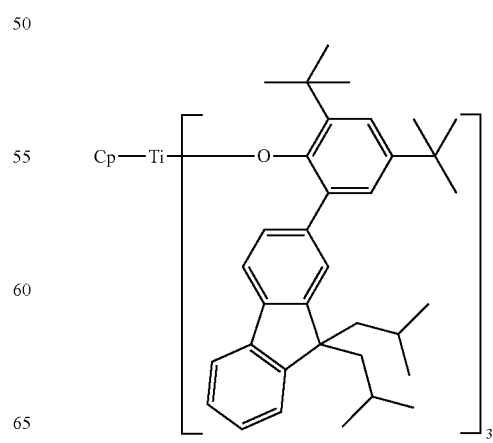

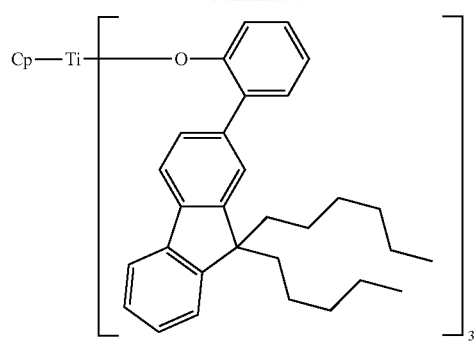
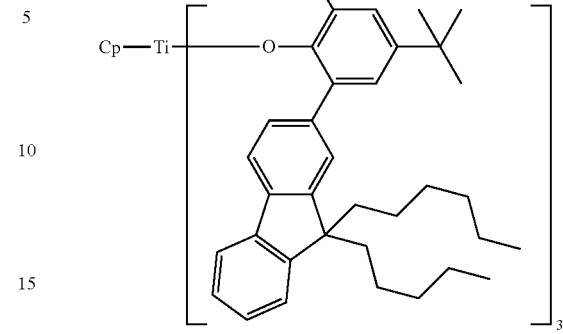
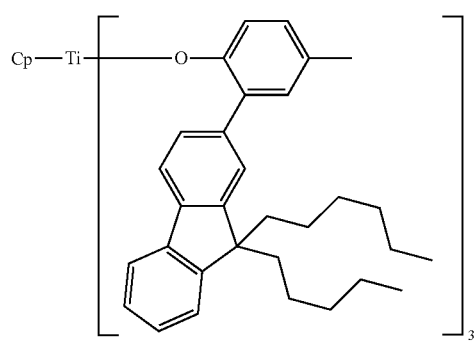
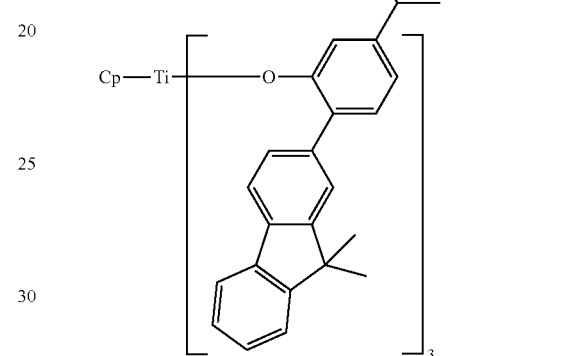
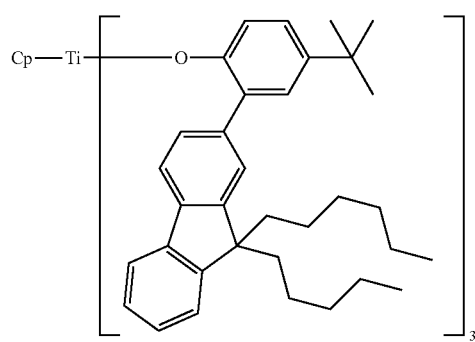
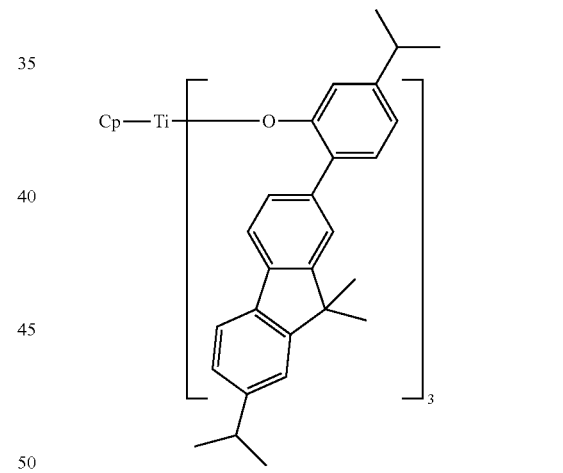
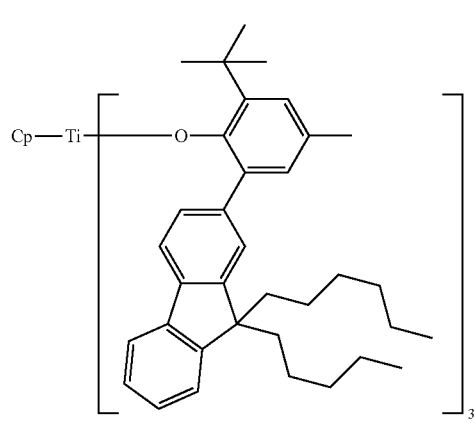
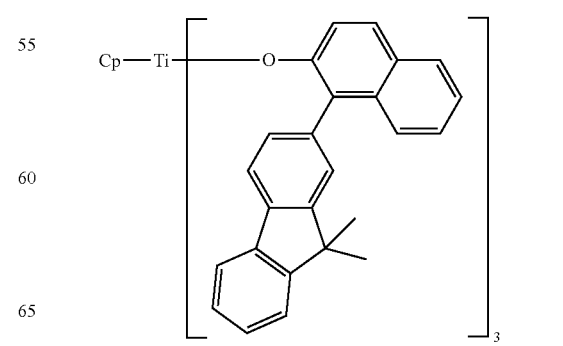

37
-continued
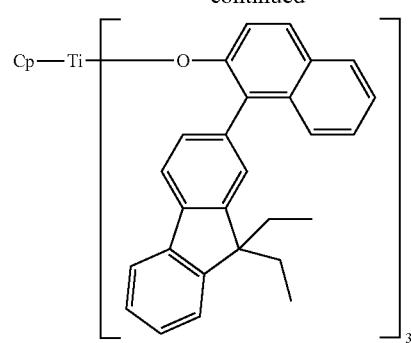
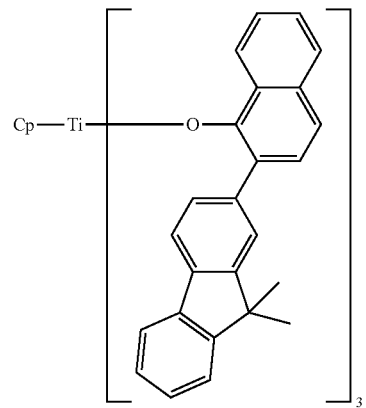
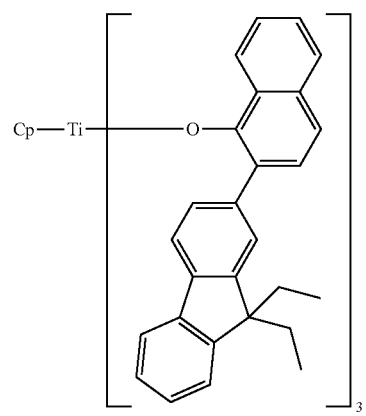
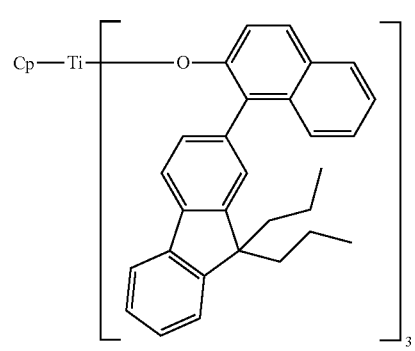
38
-continued
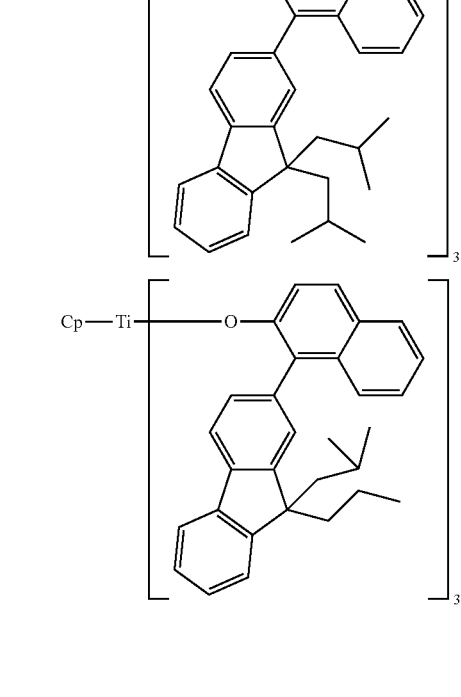
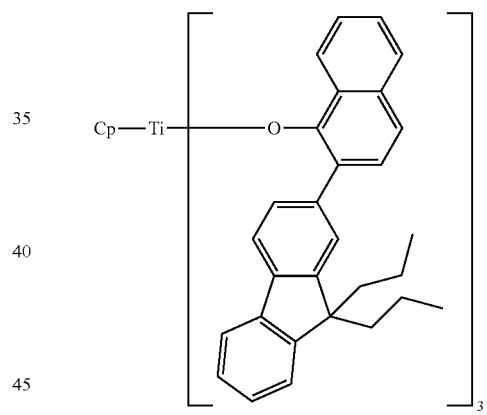
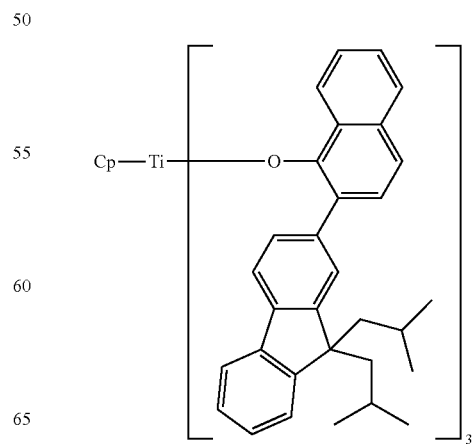

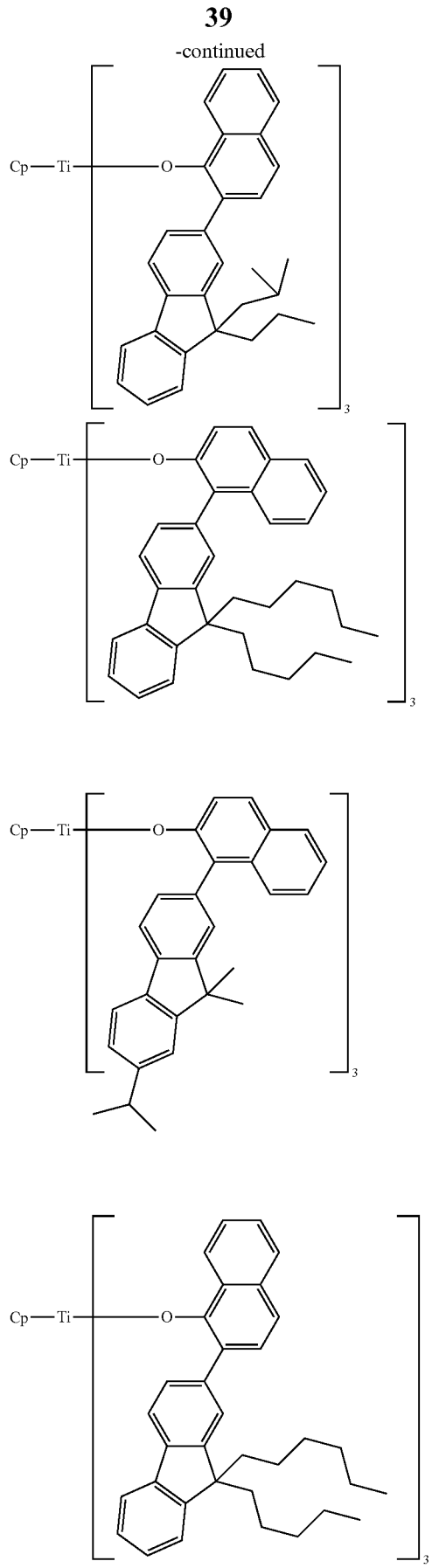

wherein, Cp is cyclopentadienyl or pentamethylcyclopentadienyl.

5. A transition metal catalyst composition for preparing an ethylene homopolymer or a copolymer of ethylene and α-olefin, the transition metal catalyst composition comprising:
 the transition metal compound of claim 1; and
 a cocatalyst selected from an aluminum compound, a boron compound, or the mixture thereof.

6. The transition metal catalyst composition of claim 5, wherein a ratio of the transition metal compound and the aluminum compound cocatalyst is in a range of 1:10 to 5,000 on the basis of a molar ratio of the transition metal (M) to aluminum (Al).

7. The transition metal catalyst composition of claim 5, wherein the aluminum compound cocatalyst, is one or a mixture of two or more selected from methylaluminoxane, modified methylaluminoxane, tetraisobutylaluminoxane, trimethylaluminum, triethylaluminum, triisobutylaluminum, and trioctylaluminum.

8. The transition metal catalyst composition of claim 5, wherein a ratio of the transition metal compound, the aluminum compound cocatalyst, and the boron compound cocatalyst is in a range of 1:0.1 to 200:10 to 1000 on the basis of a molar ratio of the transition metal (M):boron (B):aluminum (Al) atom.

9. The transition metal catalyst composition of claim 5, wherein the boron compound cocatalyst is one or a mixture of two or more selected from tris(pentafluorophenyl)borane, N,N-dimethylanilinium tetrakis(pentafluorophenyl)borate, and triphenylmethylium tetrakis(pentafluorophenyl)borate.

10. A method for preparing an ethylene homopolymer or a copolymer of ethylene and α-olefin using the transition metal catalyst composition of claim 5.

11. The method of claim 10, wherein the α-olefin polymerized with ethylene is one or a mixture of two or more selected from propylene, 1-butene, 1-pentene, 1-hexene, 1-heptene, 1-octene, 1-decene, 1-undecene, 1-dodecene, 1-tetradecene, 1-hexadecene and 1-eitosene, and a content of ethylene in the copolymer of ethylene and α-olefin is in a range of 50 to 99 wt %.

12. The method of claim 10, wherein the pressure in the reactor for ethylene homopolymer polymerization or copolymerization of ethylene and α-olefin is 1 to 1,000 atm, and the polymerization reaction temperature is 60 to 300° C.

13. The method of claim 12, wherein the pressure in the reactor for ethylene homopolymer polymerization or copolymerization of ethylene and α-olefin is 1 to 150 atm, and the polymerization reaction temperature is 80 to 250° C.

* * * * *